United States Patent
Costello et al.

(10) Patent No.: US 11,229,627 B1
(45) Date of Patent: *Jan. 25, 2022

(54) OPIOID RECEPTOR MODULATOR DOSAGE FORMULATIONS

(71) Applicant: Allergan Holdings Unlimited Company, Dublin (IE)

(72) Inventors: Tim Costello, Rockville, MD (US); Jens Jozef Ceulemans, Beerse (BE); Eugeen Maria Jozef Jans, Beerse (BE); Philip Erna H. Heyns, Beerse (BE)

(73) Assignee: Allergan Holdings Unlimited Company, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 17/507,091

(22) Filed: Oct. 21, 2021

Related U.S. Application Data

(63) Continuation of application No. 17/481,874, filed on Sep. 22, 2021, which is a continuation of application No. 17/211,274, filed on Mar. 24, 2021, now Pat. No. 11,160,792, which is a continuation of application No. 17/066,072, filed on Oct. 8, 2020, now Pat. No. 11,007,179, which is a continuation of application No. 16/795,044, filed on Feb. 19, 2020, now abandoned, which is a continuation of application No. 16/459,947, filed on Jul. 2, 2019, now abandoned, which is a continuation of application No. 16/213,083, filed on Dec. 7, 2018, now abandoned, which is a continuation of application No. 15/588,304, filed on May 5, 2017, now Pat. No. 10,188,632, which is a continuation of application No. 13/829,984, filed on Mar. 14, 2013, now Pat. No. 9,675,587.

(51) Int. Cl.

| | |
|---|---|
| *A61K 31/4174* | (2006.01) |
| *A61K 9/20* | (2006.01) |
| *A61K 47/26* | (2006.01) |
| *A61P 25/04* | (2006.01) |
| *A61K 9/50* | (2006.01) |
| *A61K 9/28* | (2006.01) |

(52) U.S. Cl.
CPC .......... *A61K 31/4174* (2013.01); *A61K 9/20* (2013.01); *A61K 9/2004* (2013.01); *A61K 9/2018* (2013.01); *A61K 9/2027* (2013.01); *A61K 9/2054* (2013.01); *A61K 9/2866* (2013.01); *A61K 9/501* (2013.01); *A61K 47/26* (2013.01); *A61P 25/04* (2018.01)

(58) Field of Classification Search
CPC .... A61K 31/4174; A61K 9/20; A61K 9/2004; A61K 9/2018
See application file for complete search history.

(56) References Cited

U.S. PATENT DOCUMENTS

| | | |
|---|---|---|
| 553,266 A | 1/1896 | Schuman |
| 3,980,766 A | 9/1976 | Shaw et al. |
| 5,312,821 A | 5/1994 | Connor et al. |
| 5,574,159 A | 11/1996 | Chang et al. |
| 6,013,658 A | 1/2000 | Lau et al. |
| 6,060,504 A | 5/2000 | Stein et al. |
| 6,518,292 B1 | 2/2003 | Robi et al. |
| 6,528,522 B2 | 3/2003 | Shih et al. |
| 7,741,356 B2 | 6/2010 | Breslin et al. |
| 7,786,158 B2 | 8/2010 | Breslin et al. |
| 7,994,206 B2 | 8/2011 | Anzalone et al. |
| 8,344,011 B2 | 1/2013 | Breslin et al. |
| 8,609,709 B2 | 12/2013 | Breslin et al. |
| 8,609,865 B2 | 12/2013 | Anzalone et al. |
| 8,691,860 B2 | 4/2014 | Anzalone et al. |
| 8,772,325 B2 | 7/2014 | Breslin et al. |
| 8,859,604 B2 | 10/2014 | Anzalone et al. |
| 9,115,091 B2 | 8/2015 | Anzalone et al. |
| 9,205,076 B2 | 12/2015 | Breslin et al. |
| 9,364,489 B2 | 6/2016 | Anzalone et al. |
| 9,675,587 B2 | 6/2017 | Costello et al. |
| 9,700,542 B2 | 7/2017 | Breslin et al. |
| 10,188,632 B2 | 1/2019 | Costello et al. |
| 11,007,179 B2 | 5/2021 | Costello et al. |
| 11,090,291 B2 | 8/2021 | Costello et al. |
| 11,160,792 B2 | 11/2021 | Costello et al. |
| 2005/0203143 A1 | 9/2005 | Breslin et al. |
| 2009/0169621 A1 | 7/2009 | Sherwood et al. |
| 2009/0263476 A1 | 10/2009 | Jobdevairakkam et al. |
| 2010/0129443 A1 | 5/2010 | Pettersson |
| 2010/0249045 A1 | 9/2010 | Babul |

(Continued)

FOREIGN PATENT DOCUMENTS

| | | |
|---|---|---|
| CN | 102786476 A | 11/2012 |
| EP | 1055655 A2 | 11/2000 |

(Continued)

OTHER PUBLICATIONS

"Formulation and Process Development for Oral Dosage Forms," 8th Annual PTI Training Program, Aug. 27-31, 2012.
Ahmad et al., "Safety and performance of current abuse-deterrent formulations," Expert Opinion on Drug Metabolism & Toxicology, 14(12): 1255-1271 (2018).
Ananthan "Opioid ligands with mixed μ/δ opioid receptor interactions: an emerging approach to novel analgesics," AAPS Journal, 8(1): E118-E125 (2006).
Bagnol et al., "Cellular localization and distribution of the cloned mu and kappa opioid receptors in rat gastrointestinal tract," Neuroscience, 81(2): 579-591 (1997).
Balboni et al., "Opioid pseudopeptides containing heteroaromatic or heteroaliphatic nuclei," Peptides, 21(11): 1663-1671 (2000).
Barber, A. et al., A pharmacological profile of the novel, peripherally-selective k-opioid receptor agonist, EMD 61753, Br. J. Pharmacol., 113:1317-1327 (1994).

(Continued)

*Primary Examiner* — Mark V Stevens
(74) *Attorney, Agent, or Firm* — Foley Hoag LLP

(57) ABSTRACT

Abuse deterrent solid dosage formulations containing 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid, and processes for the preparation and administration of these formulations.

30 Claims, 2 Drawing Sheets

(56) References Cited

U.S. PATENT DOCUMENTS

| | | | |
|---|---|---|---|
| 2010/0324051 A1* | 12/2010 | Breslin | A61P 25/00 514/249 |
| 2011/0002985 A1 | 1/2011 | Shah et al. | |
| 2012/0065221 A1 | 3/2012 | Babul | |
| 2012/0214820 A1 | 8/2012 | Kalyankar et al. | |
| 2012/0282336 A1 | 11/2012 | Abebe et al. | |
| 2014/0256779 A1 | 9/2014 | Breslin et al. | |
| 2014/0271854 A1 | 9/2014 | Costello et al. | |
| 2016/0030393 A1 | 2/2016 | Breslin et al. | |
| 2016/0354389 A1 | 12/2016 | Anzalone et al. | |
| 2017/0304268 A1 | 10/2017 | Costello et al. | |
| 2021/0205268 A1 | 7/2021 | Costello et al. | |
| 2021/0205269 A1 | 7/2021 | Costello et al. | |

FOREIGN PATENT DOCUMENTS

| | | |
|---|---|---|
| EP | 1208143 A1 | 5/2002 |
| EP | 2653465 A1 | 10/2013 |
| WO | WO-02/36116 A2 | 5/2002 |
| WO | WO-03/033486 A1 | 4/2003 |
| WO | WO-03/092688 A2 | 11/2003 |
| WO | WO-2003097051 A2 | 11/2003 |
| WO | WO-2005/053587 A1 | 6/2005 |
| WO | WO-2005/090315 A1 | 9/2005 |
| WO | WO-2007/043061 A1 | 4/2007 |
| WO | WO-2008068471 A1 | 6/2008 |
| WO | WO-2009122431 A2 | 10/2009 |
| WO | WO-2010/132431 A1 | 11/2010 |

OTHER PUBLICATIONS

Barber, Andrew et al., "Review: Central & Peripheral Nervous Systems—Novel developments with selective, non-peptidic kappa-opioid receptor agonists," Expert Opinion on Investigational Drugs, 6(10): 1351-1368 (1997).

Binder et al., "Effect of the peripherally selective K-opioid agonist, asimadoline, on adjuvant arthritis," Br. J. of Pharmacol., 124(4): 647-654 (1998).

Bitar et al., "Specific opiate receptors on isolated mammalian gastric smooth muscle cells," Nature, 297(5861): 72-74 (1982).

Black et al., "The kappa opioid receptor is associated with the perception of visceral pain," Gut, 43: 312-313(1998).

Brandt et al., "An evidence-based position statement on the management of irritable bowel syndrome", The American journal of gastroenterology, 104(Suppl 1): S1-S35 (2009).

Breslin et al., "Identification of a dual δ or antagonist/µ agonist as a potential therapeutic for diarrhea-predominant irritable bowel syndrome (IBS-d)," Bioorganic & Medicinal Chemistry Letters, 22(14): 4869-4872 (2012).

Callahan, Michael J., "Irritable Bowel Syndrome Neuropharmacology: A Review of Approved and Investigational Compounds," J. of Clinical Gastroenterology, 35(Suppl. 1): S58-S67 (2002).

Camilleri, M. et al., "Consensus report: clinical perspectives, mechanisms, diagnosis and management of irritable bowel syndrome," Alimentary Pharmacol. & Therap., 16: 1407-1430 (2002).

Camilleri, M. et al., "Visceral hypersensitivity: facts, speculations, and challenges," Gut, 48: 125-131 (2001).

Camilleri., Michael, "Management of the irritable bowel syndrome," Gastroenterology, 120(3): 652-668 (2001).

Clinical Trial NCT01130272 (As of Mar. 13, 2012)—Efficacy, Safety, and Tolerability of JNJ-27018966 in the Treatment of Irritable Bowel Syndrome With Diarrhea; Last Accessed Aug. 24, 2021.

Clinical Trial NCT01553747 (As of Mar. 7, 2012)—Efficacy, Safety, and Tolerability of JNJ-27018966 in the Treatment of Patients With Diarrhea-Predominant Irritable Bowel Syndrome (Protocol JNJ-27018966IBS3002); Last Accessed Aug. 24, 2021.

Coleman et al., "New Pharmaceutical Approaches to the Treatment of IBS: Future Development & Research," Annals of Gastro, 15(3): 278-279 (2002).

Colorcon, Opadry II, Application Data sheet, Aug. 2009.

Corazziari, Enrico, et al., "Gut Dysfunction in IBS: Role of opioid ligands in irritable bowel syndrome," Canadian J. of Gastroenterol., 13(Supp. A): 71A-75A (1999).

De Schepper, H.U., et al., "Review: Opioids and the gut: pharmacology and current clinical experience," Neurogastroenterol. Motil 16:383-394 (2004).

Delgado-Aros et al., "Effects of a -opioid agonist, asimadoline, on satiation and Gl motor and sensory functions in humans," Am. J. Physiol. Gastrointest. Liver Physiol., 284: G558-G566 (2003).

Delvaux, M., et al., "Effect of asimadoline, a K opioid agonist, on pain induced by colonic distension in patients with irritable bowel syndrome," Aliment Pharmacol. Ther., 20: 237-246 (2004).

Dietis et al., "Simultaneous targeting of multiple opioid receptors: a strategy to improve side-effect profile," British Journal of Anaesthesia, 103 (1): 38-49 (2009).

Dokray, "Physiology of Enteric Neuropeptides," in Johnson LR ed Physiology of the Gastrointestinal Track 3rd ed New York Raven, 1194, 169-209 (1994).

Drossman "The functional gastrointestinal disorders and the Rome III process," Gastroenterology, 130(5): 1377-1390 (2006).

Drossman, Rome III the Functional GI Disorders, 3rd Edition, Lawrence: Allen Press Inc., 2006.

Dufour, E., et al., "Synthesis of amidrazones using an engineered papain nitrile hydratase," FEBS Letters, 433: 78-82 (1998).

Extended European Search Report for EP Application No. 20125626.1 dated Jul. 9, 2021.

Extended Search Report for European Patent Application No. 14774006.2, dated Jul. 26, 2016 12 pages.

Holzer, "Opioid receptors in the gastrointestinal tract," Regulatory Peptides, 155(1-3): 11-17 (2009).

International Preliminary Report on Patentability for International (PCT) Patent Application No. PCT/US2014/022666, dated Sep. 24, 2015 12 pages.

International Search Report and Written Opinion for International (PCT) Patent Application No. PCT/US2014/022666, dated Jul. 9, 2014 14 pages.

Joshi, S.K., et al., "K-Opioid Receptor Agonists Modulate Visceral Nociception at a Novel, Peripheral Site of Action," J. of Neurosciene, 20(15): 5874-5829 (2000).

Kamel et al., "Pharmaceutical significance of cellulose: A review," eXPRESS Polymer Letters, 2(11): 758-778 (2008).

Liu, Bao-Hua, et al., "Effects of mu and kappa opioid receptor agonists and antagonists on contraction of isolated colon strips of rats with cathartic colon," World J. Gastroenterol., 10(11): 1672-1674 (2004).

Lovell et al., "Global prevalence of and risk factors for irritable bowel syndrome: a meta-analysis," Clinical gastroenterology and hepatology, 10(7): 712-721 (2012).

Malagelada, J.-R., "Review article: clinical pharmacology models of irritable bowel syndrome," Alimentary Pharmacol. & Therap., 13(Supp. 2): 57-64 (1999).

Mertz, H., "Review article: visceral hypersensitivity," Alimentary Pharm & Therap., 17(5): 623-633 (2003).

Non Final Office Action dated Feb. 7, 2017 for U.S. Appl. No. 13/829,984, filed Mar. 14, 2013.

Non Final Office Action dated Jan. 8, 2015 for U.S. Appl. No. 14/459,514, filed Aug. 14, 2014.

Non Final Office Action dated Jul. 12, 2016 for U.S. Appl. No. 13/829,984, filed Mar. 14, 2013.

Non Final Office Action dated Jun. 16, 2014 for U.S. Appl. No. 14/282,828, filed May 20, 2014.

Non Final Office Action dated Sep. 17, 2014 for U.S. Appl. No. 13/829,984, filed Mar. 14, 2013.

Non Final Office Action dated Jun. 30, 2015 for U.S. Appl. No. 13/829,984, filed Mar. 14, 2013.

Non Final Office Action dated Dec. 31, 2015 for U.S. Appl. No. 13/829,984, filed Mar. 14, 2013.

Notice of Allowance for U.S. Appl. No. 13/829,984, dated Feb. 7, 2017.

Official Action for Eurasia Patent Application No. 201591768, dated May 16, 2017 4 pages.

(56) References Cited

OTHER PUBLICATIONS

Official Action with English Translation for China Patent Application No. 201480026522.7, dated Jan. 13, 2017 23 pages.
Official Action with English Translation for Eurasia Patent Application No. 201591768, dated Oct. 5, 2016 5 pages.
Ozaki, Noriyuki, et al., "Differential Effects of μ-, δ-, and K-Opioid Receptor Agonists on Mechanosensitive Gastric Vagal Afferent Fibers in the Rat," The Am. Physiological Society, 83(4): 2209-2216 (1999).
P&T Product Profiler., "Abstral® Fentanyl Sublingual Tablets for Breakthrough Cancer Pain," vol. 36, Issue 2 Section Three: 30 pages (2011).
Porreca et al., "Potential for Development of Novel Analgesic Agents," Pain: Understanding, Emerging Therapies, and Novel Approaches to Drug Discovery, 407-419 (1st Ed. Taylor & Francis Group LLC) (2003).
Raval and Patel, "Silicified Microcrystalline Cellulose as a Multifunctional Pharmaceutical Excipient," Drug Delivery Technology, Apr. 2009 vol. 9 No 4 pp. 28-32.
Reynolds, James C., "Challenges in the treatment of colonic motility disorders," Am. J. Health-System Pharmacy, 53(Supp 3): S17-S26 (1996).
Riviere et al., "Opioid Receptors: Targets for New Gastrointestinal Drug Development," Drug Development: Molecular Targets for GI Diseases p. 203-38 (Gaginella, T.S., and Guglietta, A., Eds. 2000).
Riviere, Pierre J.-M., "Review: peripheral kappa-opioid agonists for visceral pain," Br. J. of Pharm., 141: 1331-1334 (2004).
Schreiber, Rainer, et al., "The δ-opioid receptor agonist asimadoline inhibits epithelial transport in mouse trachea and colon," Eur. J. of Pharmacol., 503(1-3): 185-190 (2004).
Talley, Nicholas J., "Evaluation of drug treatment in irritable bowel syndrome," Br. J. Clin. Pharmacol., 56(4): 362-369 (2003).
Talley, Nicholas J., "Irritable Bowel Syndrome: Physiology and Management," Medscape Gastroenterology (posted Jun. 7, 2002).
The Handbook of Pharmaceutical Excipients (5th ed. 2006), published by the American Pharmaceutical Association and the Pharmaceutical Society of Great Britain.
Truberzi Summary of Product Characteristics dated Sep. 19, 2016.
U.S. Appl. No. 14/459,514, filed Aug. 14, 2014, Anzalone et al.
Wade et al., "Modulation of gastrointestinal function by MuDelta, a mixed .μ.opioid receptor agonist/ .μ. opioid receptor antagonist," British Journal of Pharmacology, 167(5): 1111-1125 (2012).
Zhang Xingfang "Performance Manual of the Raw Materials of Foreign Propellants and Explosives," Weapon Industry Press, Nov. 1991, p. 283, 3 pages.

* cited by examiner

OPIOID RECEPTOR MODULATOR DOSAGE FORMULATIONS

CROSS-REFERENCE TO RELATED APPLICATIONS

This application is a continuation of U.S. patent application Ser. No. 17/481,874, filed Sep. 22, 2021; which is a continuation of U.S. patent application Ser. No. 17/211,274, filed Mar. 24, 2021; which is a continuation of U.S. patent application Ser. No. 17/066,072, filed Oct. 8, 2020; which is a continuation of U.S. patent application Ser. No. 16/795,044, filed Feb. 19, 2020; which is a continuation of U.S. patent application Ser. No. 16/459,947, filed Jul. 2, 2019; which is a continuation of U.S. patent application Ser. No. 16/213,083, filed Dec. 7, 2018; which is a continuation of U.S. patent application Ser. No. 15/588,304, filed May 5, 2017; which is a continuation of U.S. patent application Ser. No. 13/829,984, filed Mar. 14, 2013. The disclosures of the foregoing references are hereby incorporated by reference in their entireties.

FIELD OF THE DISCLOSURE

The present disclosure relates to oral dosage formulations containing 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid, and processes for the preparation and administration of these formulations.

BACKGROUND OF THE DISCLOSURE

Delivering an active pharmaceutical ingredient ("5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid") to a patient requires more than just identifying a molecule and its use. An 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid must be formulated for delivery to a patient and this formulation (in addition to the 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid activity) is evaluated by regulatory agencies such as the US Food and Drug Administration (FDA) and the European Medicines Agency (EMA). The FDA evaluates the formulation for, among other properties, delivery properties, stability, consistency, and manufacturing controls. An important factor in determining these properties of a particular formulation is the composition and form of the dosage formulation of the 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid. The formulations for every 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid are different and different formulations containing the same 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid may have very different stability and drug delivery (e.g., pharmacokinetic) properties.

5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid is an opioid receptor modulator that effects simultaneous agonism of the μ opioid receptor (MOR) and antagonism of the δ opioid receptor (DOR) and may be useful in the treatment and prevention of various mammalian disease states, for example pain and gastrointestinal disorders such as diarrheic syndromes, motility disorders including post-operative ileus and constipation, and visceral pain including post-operative pain, irritable bowel syndrome and inflammatory bowel disorders (for example, see U.S. Pat. No. 7,741,356 to Breslin, et al., which is incorporated herein in its entirety). Irritable bowel syndrome is a common functional gastrointestinal disorder that affects approximately 10-15% of the population in western countries (Lovell et al., Clin Gastroenterol Hepatol 2012; 10(7):712-21). Irritable bowel syndrome is characterized by recurrent abdominal discomfort and pain associated with altered bowel habits (Drossman D A, Gastroenterol 2006; 130(5):1377-1390). Currently irritable bowel syndrome subtypes include diarrhea (IBS-D), constipation (IBS-C), or mixed constipation and diarrhea (IBS-M). Irritable bowel syndrome can negatively impact individual's quality of life and results in significant direct and indirect costs (Drossman D A. Rome III The Functional GI Disorders. $3^{rd}$ Edition. Lawrence: Allen Press, Inc, 2006). Current safe and effective pharmacologic treatments for IBS-D are limited and include antispasmodics, antidepressants, antidiarrheal agents, and alosetron (Brandt et al., Am J Gastroenterol 2009; 104(Suppl 1):S1-35).

Opioid receptors, including mu, delta, and kappa are expressed along the gastrointestinal tract and play a key role in regulating gastrointestinal motility, secretion and visceral sensation (Bagnol et al., Neuroscience 1997; 81(2):579-591; Dokray G J, Physiology of Enteric Neuropeptides. In: Johnson L R ed. Physiology of the Gastrointestinal Tract. $3^{rd}$ ed. New York: Raven, 1994; 169-209; Bitar et al., Nature 1982; 297(5861):72-74). Exogenous opioids reduce gastrointestinal transit through activation of MOR and can treat diarrhea in acute situations (Holzer P., Regulatory Peptides 2009; 155:11-17). Agents that simultaneously activate MOR while antagonizing DOR have differential gastrointestinal effects and may possess increased analgesic potency compared to pure MOR agonists (Ananthan S. Opioid ligands with mixed μ/δ opioid receptor interactions: an emerging approach to novel analgesics. AAPS Journal 2006; 8(1):E118-E125; Dietis et al., British Journal of Anaesthesia 2009; 103(1):38-49). Such a mixed MOR agonist/DOR antagonist profile may offer an advantage in treating both the diarrhea and abdominal pain associated with IBS-D.

5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid may be particularly useful for reducing pain and diarrhea in patients with irritable bowel syndrome with diarrhea (IBS-D) without constipating side effects. In vitro, it reduces contractility in intestinal tissue and inhibits neurogenically-mediated secretion (Wade et al., Br J Pharmacol 2012; 167(5):1111-1125). In vivo, it reduces gastrointestinal transit and fecal output in stressed and non-stressed mice over a wide dose-range without fully inhibiting gastrointestinal transit (ibid.). In contrast, loperamide had a narrow dose range in the same stressed and non-stressed models and completely prevented fecal output in a dose-dependent manner (ibid.).

5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid and methods of making this molecule are disclosed in U.S. Pat. No. 7,741,356. Example 9 of U.S. Pat. No. 7,741,356 makes the hydrochloride salt of 5-({[2-amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid. Applicants have also discovered a process of making the zwitterion of 5-({[2-amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid and two novel crystals of this zwitterions (for example, see U.S. Patent Publication No. 2011/0263868 to Anzalone, et. al., which is incorporated herein in its entirety).

Oral administration of 5-({[2-amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid is efficacious in normalizing gastrointestinal (GI) motility in stressed subjects and providing anti-visceral hyperalgesic effects in rats by acting at peripheral opioid receptors in the gastrointestinal tract. It has also been noted that parenteral administration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid results in CNS-related effects in animal models, which is believed to be due to the mu-opioid receptor ("MOR") agonist properties.

The recent draft guidance issued for industry by the US Food and Drug Administration (Food and Drug Administration 2010) for the assessment of abuse potential of drugs provides general instructions for in vitro laboratory assessment procedures. This draft guidance states that "[i]nformation should be obtained on how much drug substance might be released and any changes that could take place in the rate of release of the drug from the drug product if it is misused either intentionally or unintentionally." The guidance further states that the "effects of pH, temperature, and solvent polarity on disruption of the drug product matrix should be evaluated. Additional experimental variables may include exposure times to the solvent, agitation, varying the surface area (such as from intact to being ground, crushed, or cut into pieces), and ease of crushing tablets or destroying the dosage from matrix." These guidelines pertain to compounds perceived to have any potential for abuse, misuse and/or diversion, which include, but are not limited to, opioid receptor agonists. The goal is to determine the effects that certain formulations may have in limiting or preventing abuse of the active ingredient, in this instance, 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid, in order to decrease abuse or diversion of the marketed dosage formulations and prevent harm and addiction in the public to the extent possible.

Therefore an abuse liability assessment of oral dosage formulations of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid was undertaken to identify oral formulation compositions and characteristics that may provide effective treatment of opioid receptor disorders while minimizing or elimination potential for abuse or diversion of these oral formulations.

SUMMARY OF DISCLOSURE

The present inventors have discovered solid oral pharmaceutical formulations of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid with improved stability and shelf life and unique physico-chemical features that may deter or limit abuse of the active ingredient or diversion of the oral formulations. Thus, embodiments provided by this disclosure include an abuse deterrent pharmaceutical formulation of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid.

One embodiment of the disclosure provides a solid pharmaceutical formulation comprising 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid and an inert ingredient selected from silicified microcrystalline cellulose, colloidal silicon dioxide, crospovidone (polyvinylpolypyrrolidone; highly cross-linked polyvinylpyrrolidone (PVP)), mannitol, and magnesium stearate. In a specific embodiment, this pharmaceutical formulation may be substantially or completely free of a separate opioid antagonist, such as naloxone. A related embodiment provides a pharmaceutical formulation consisting of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid and an inert ingredient selected from silicified microcrystalline cellulose, colloidal silicon dioxide, crospovidone, mannitol, and magnesium stearate.

One embodiment of the disclosure provides a solid pharmaceutical formulation comprising 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid and inert ingredients including silicified microcrystalline cellulose, colloidal silicon dioxide, crospovidone (polyvinylpolypyrrolidone; highly cross-linked polyvinylpyrrolidone (PVP)), mannitol, and magnesium stearate. In a specific embodiment, this pharmaceutical formulation may be substantially or completely free of a separate opioid antagonist, such as naloxone. A related embodiment provides a pharmaceutical formulation consisting of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid, and the inert ingredients silicified microcrystalline cellulose, colloidal silicon dioxide, crospovidone, mannitol, and magnesium stearate.

One embodiment of the disclosure provides a solid oral dosage formulation comprising 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid and an inert ingredient selected from silicified microcrystalline cellulose, colloidal silicon dioxide, crospovidone (polyvinylpolypyrrolidone; highly cross-linked polyvinylpyrrolidone (PVP)), mannitol, and magnesium stearate. In a specific embodiment, this solid oral dosage formulation may be substantially or completely free of a separate opioid antagonist, such as naloxone. A related embodiment provides a solid oral dosage formulation consisting of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid and an inert ingredient selected from silicified microcrystalline cellulose, colloidal silicon dioxide, crospovidone, mannitol, and magnesium stearate. In these embodiments, the oral dosage formulations may be coated, including sugar coated, gelatin coated, film coated or enteric coated, by standard techniques.

Another embodiment of the disclosure provides an oral tablet formulation comprising 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid and an inert ingredient selected from silicified microcrystalline cellulose, colloidal silicon dioxide, crospovidone (polyvinylpolypyrrolidone; highly cross-linked polyvinylpyrrolidone (PVP)), mannitol, and magnesium stearate. In a specific embodiment, this oral tablet formulation may be substantially or completely free of a separate opioid antagonist, such as naloxone. A related embodiment provides an oral tablet formulation consisting of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid and an inert ingredient selected from silicified microcrystalline cellulose, colloidal silicon dioxide, crospovidone, mannitol, and magnesium stearate. In these embodiments, the oral tablet formulations may be coated, including sugar coated, gelatin coated, film coated or enteric coated, by standard techniques.

Another embodiment of the disclosure provides a film-coated, oral tablet formulation comprising 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid and an inert ingredient selected from silicified microcrystalline cellulose, colloidal silicon dioxide, crospovidone (polyvinylpolypyrrolidone; highly cross-linked polyvinylpyrrolidone (PVP)), mannitol, and magnesium stearate, and a film coating. In a specific embodiment, this film-coated, oral tablet formulation may be substantially or completely free of a separate opioid antagonist, such as naloxone. A related embodiment provides a film-coated, oral tablet formulation consisting of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid and an inert ingredient selected from silicified microcrystalline cellulose, colloidal silicon dioxide, crospovidone, mannitol, and magnesium stearate, and a film coating. In these embodiments, the film coating may be an aqueous film coating.

A specific embodiment is an abuse deterrent, mono-phasic pharmaceutical composition suitable for single dose administration for treating or ameliorating a condition mediated by an opioid receptor consisting essentially of about 20 mg/dose to about 200 mg/dose of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid, from about 60-80% by weight of silicified microcrystalline cellulose, from about 2-8% by weight of colloidal silica, from about 50-90% by weight of mannitol, from about 20-50% by weight of crospovidone, and from about 2-8% by weight of magnesium stearate.

Another embodiment provided by this disclosure is a method of treating or ameliorating a condition mediated by an opioid receptor by administering 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid in a solid oral formulation of this disclosure to a subject in need of such treatment. In a specific embodiment, this administration may be made in the absence of the separate or concurrent administration of an opioid antagonist, such as naloxone. In specific embodiments, these methods may include the administration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid to the subject in an amount between 20 mg and 200 mg.

In specific embodiments, these methods may include the administration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid to the subject in an amount between about 10 mg and about 125 mg. In specific embodiments, these methods may include the administration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid to the subject in an amount between about 50 mg and about 100 mg.

In specific embodiments, these methods may include the administration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid to the subject in an amount of about 75 mg. In specific embodiments, these methods may include the administration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid to the subject in an amount of about 100 mg.

In specific embodiments, these methods may include the administration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid in a formulation of this disclosure to the subject between two administrations per day and eight administrations per day. In specific embodiments, these methods may include the administration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid in a formulation of this disclosure to the subject between two administrations per day and six administrations per day. In specific embodiments, these methods may include the administration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid in a formulation of this disclosure to the subject between two administrations per day and four administrations per day. In specific embodiments, these methods may include the administration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid in a formulation of this disclosure to the subject on a twice-daily dosing regimen. In specific embodiments, these methods may include the administration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid in a formulation of this disclosure to the subject on a once-daily dosing regimen.

This Summary of the Disclosure is neither intended nor should it be construed as being representative of the full extent and scope of the present disclosure. Moreover, references made herein to "the present disclosure," or aspects thereof, should be understood to mean certain embodiments of the present disclosure and should not necessarily be construed as limiting all embodiments to a particular description. The present disclosure is set forth in various levels of detail in the Summary of the Disclosure as well as in the attached drawings and the Description of Embodiments and no limitation as to the scope of the present disclosure is intended by either the inclusion or non-inclusion of elements, components, etc. in this Summary of the Disclosure. Additional aspects of the present disclosure will become more readily apparent from the Description of Embodiments, particularly when taken together with the drawings.

DESCRIPTION OF ILLUSTRATIVE EMBODIMENTS

Figure 1:
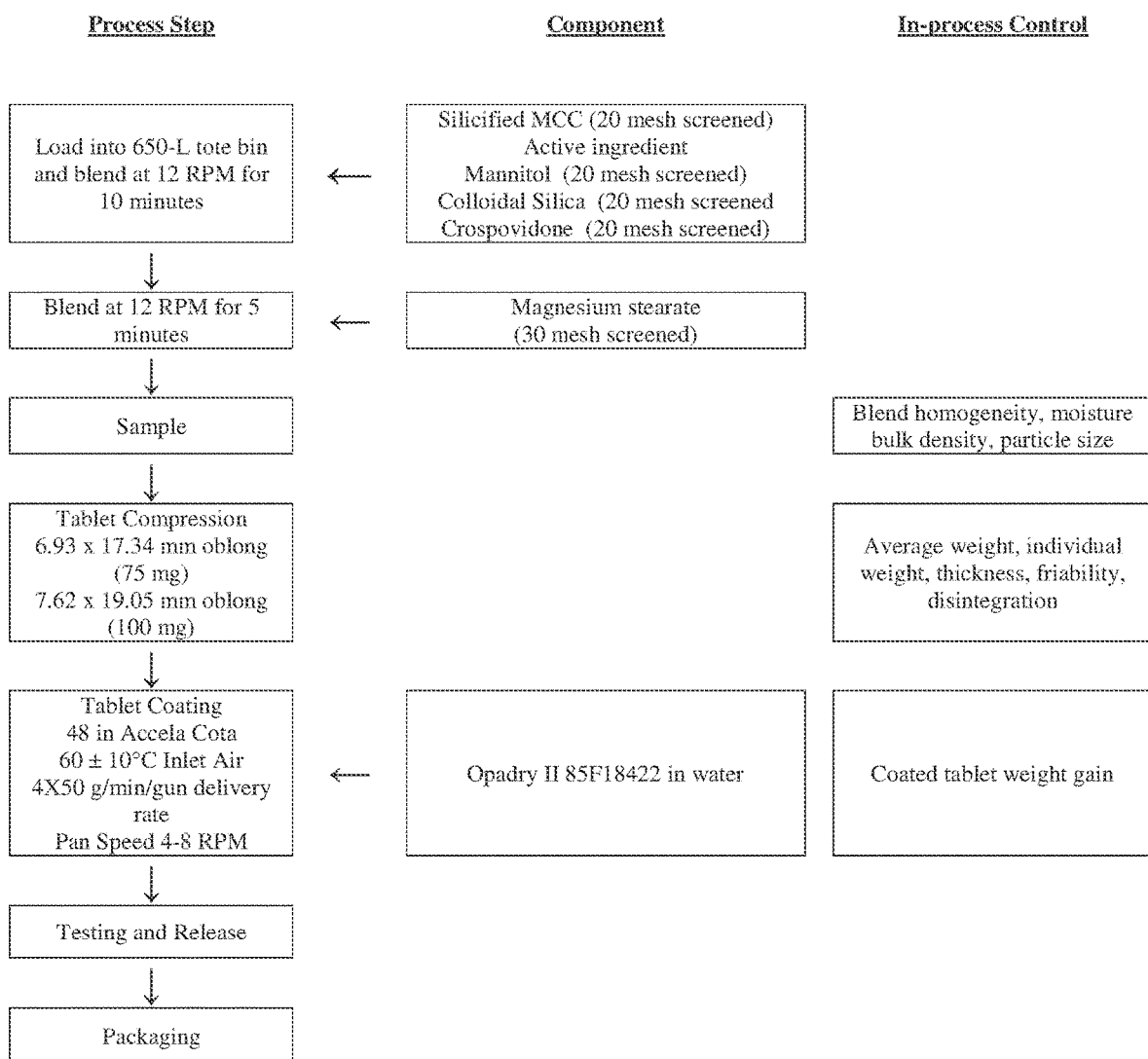
FIG. 1 depicts the manufacturing process for 75-mg and 100-mg oral tablets of the present disclosure.

The present disclosure is drawn to solid dosage formulations containing 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid that deter or minimize the abuse or diversion of these formulations, as well as processes for the preparation and administration of these formulations.

For the purposes of this disclosure, reference to "5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid" also means "5-[[[-2-amino-3-[4-(aminocarbonyl)-2,6-dimethylphenyl]-1-oxopropyl][-1-(4-phenyl-1H-imidazol-2-yl)ethyl]amino]methyl]-2-methoxybenzoic acid", and it is intended that the two chemical names can be used interchangeably. Reference to the "active ingredient" includes 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid, and pharmaceutically acceptable enantiomers, diastereomers, racemates, zwitterions, and salts thereof.

Because 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid includes at least two chiral centers, it may exist as diastereomers. These isomers may be separated by conventional techniques such as preparative chromatography and may be prepared in racemic form or as individual diastereomers by either stereo-specific synthesis or by resolution. The compounds may, for example, be resolved into their component diastereomers by standard techniques, such as the formation of stereoisomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers and enantiomers are encompassed within the scope of any reference to "5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid" or the "active ingredient" in this disclosure.

For example, reference to "5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid" or the "active ingredient" specifically includes:

a) 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid, b) 5-({[(2S)-2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid, c) 5-({[2-Amino-3-(4-carbamoyl-2,6-dimethyl-phenyl)-propionyl]-[(1S)-1-(4-phenyl-1H-imidazol-2-yl)-ethyl]-amino}-methyl)-2-methoxy-benzoic acid, and/or d) 5-({[(2S)-2-Amino-3-(4-carbamoyl-2,6-dimethyl-phenyl)-propionyl]-[(1S)-1-(4-phenyl-1H-imidazol-2-yl)-ethyl]-amino}-methyl)-2-methoxy-benzoic acid, as well as e) a hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid salt of any one of these compounds, or f) a benzathine, chloroprocaine, choline, diethanolamine, ethylenediamine, meglumine, procaine, aluminum, calcium, lithium, magnesium, potassium, sodium, or zinc salt of any one of these compounds.

Similarly, reference to "5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid" or the "active ingredient" specifically includes a compound having the chemical structure:

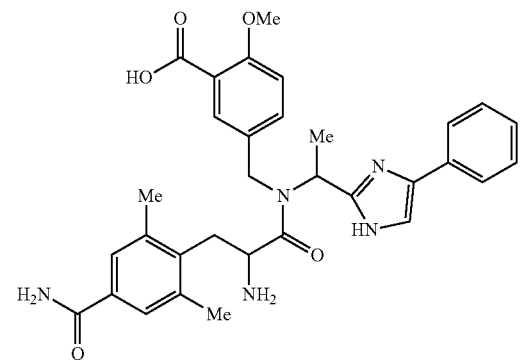

, and/or

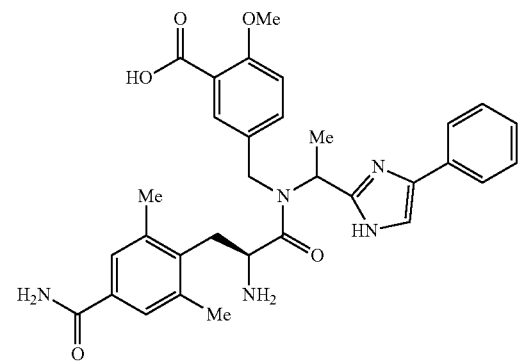

, and/or

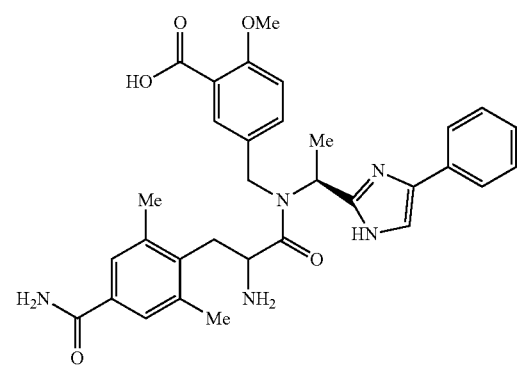

, and/or

-continued

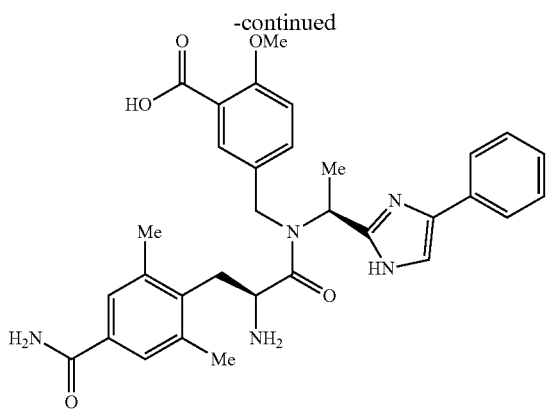

as well as a hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid salt, or a benzathine, chloroprocaine, choline, diethanolamine, ethylenediamine, meglumine, procaine, aluminum, calcium, lithium, magnesium, potassium, sodium, or zinc salt of any one of these chemical structures.

As used in this disclosure, the terms "subject," "patient," "individual," etc. are not intended to be limiting and can be generally interchanged. That is, an individual described as a "patient" does not necessarily have a given disease, but may be merely seeking medical advice.

As used herein, the terms "treat" and "prevent" are not intended to be absolute terms. Treatment can refer to any delay in onset, reduction in the frequency or severity of symptoms, amelioration of symptoms, improvement in patient comfort and/or gastrointestinal function, etc. The effect of treatment can be compared to an individual or pool of individuals not receiving a given treatment, or to the same patient prior to, or after cessation of, treatment.

The term "prevent" or "ameliorate" refers to a decrease in the occurrence of opioid receptor disease or disorder symptoms in a patient. The prevention or amelioration may be complete (no detectable symptoms) or partial, such that fewer symptoms are observed than would likely occur absent treatment.

The phrase "opioid receptor related disorders" refers to various mammalian disease states including, for example, pain and gastrointestinal disorders such as diarrheic syndromes, motility disorders including post-operative ileus and constipation, and visceral pain including post-operative pain, irritable bowel syndrome and inflammatory bowel disorders, as described in greater detail in U.S. Pat. No. 7,741,356 to Breslin, et al., which is incorporated herein in its entirety.

The term "abusive" or "abusive manner" refers to uses of the formulations of this disclosure beyond oral administration, such as by injecting or snorting.

The term "abuse deterrent", as used herein, refers to a formulation of the present invention which possesses physico-chemical characteristics that allow the therapeutic use of the opioid receptor modulator active ingredient by oral administration to a subject in need of such treatment with very limited potential for abuse or misuse of the formulation, i.e., by extracting and ingesting the active ingredient by snorting or injection.

The term "therapeutically effective amount," as used herein, refers to that amount of the therapeutic agent sufficient to treat or ameliorate the disease or disorder, as described above. For example, for the given parameter, a therapeutically effective amount will show an increase or decrease of at least about 5%, 10%, 15%, 20%, 25%, 30%, 40%, 50%, 60%, 70%, 80%, 90%, or 100%. Therapeutic efficacy can also be expressed as "-fold" increase or decrease. For example, a therapeutically effective amount can have at least a 1.2-fold, 1.5-fold, 2-fold, 5-fold, or more effect over a control value. Therapeutic efficacy related to irritable bowel syndrome, preferably diarrhea-predominant irritable bowel syndrome, can be expressed in measurements of worst abdominal pain (WAP) or stool consistency score (Bristol Stool Scale or BSS).

The term "solid dosage formulation" as used herein includes tablets, capsules, pills and like and may be present as conventional or extended-release compositions.

The terminology used herein is for describing particular embodiments and is not intended to be limiting. As used herein, the singular forms "a," "and" and "the" include plural referents unless the content and context clearly dictate otherwise. Thus, for example, a reference to "a marker" includes a combination of two or more such markers. Unless defined otherwise, all scientific and technical terms are to be understood as having the same meaning as commonly used in the art to which they pertain. For the purposes of the present disclosure, the following terms are defined below.

Also, the use of "or" means "and/or" unless stated otherwise. Similarly, "comprise," "comprises," "comprising," "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

In some embodiments related to the treatment of opioid receptor related disorders, the dose of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid that can be incorporated into the formulations of the present disclosure depends on the desired treatment dosage to be administered and can range from about 20 mg to about 200 mg of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid. In other embodiments, the dose of the active ingredient can range from about 10 mg to about 125 mg. In some embodiments, the dose of the active ingredient in the formulations of this disclosure is between about 10 mg and about 200 mg, e.g., 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid. In one embodiment, the dose is about 75 mg of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid. In another embodiment, the dose is about 100 mg of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid. In another embodiment, the dose is about 50 mg of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid. In yet another embodiment, the dose is about 150 mg of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid. In yet another embodiment, the dose is about 37.5 mg of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid.

Dose proportionality occurs when increases in the administered dose are accompanied by proportional increases in a pharmacokinetic parameter. The dosage formulations of the present disclosure are preferably designed as a dose proportional formulation in the range of 25 mg to 100 mg of the active ingredient 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid.

Abuse deterrent formulations of the present invention include solid pharmaceutical dosage formulations containing:

from about 5-20% by weight of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid, preferably from about 10-15% by weight of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid, preferably about 12.5% by weight of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid;

from about 60-80% by weight of silicified microcrystalline cellulose (USP Silicified Microcrystalline Cellulose; intimately associated microcrystalline cellulose and colloidal silicon dioxide particles; in a preferred example, high density silicified microcrystalline cellulose "HD-90"); preferably from about 65-75% by weight of silicified microcrystalline cellulose, preferably about 71% by weight of silica fine microcrystalline cellulose;

from about 0.45-1.0% by weight of a glidant, e.g., colloidal silica, preferably from about 0.55-0.95% by weight of colloidal silica, in one preferred embodiment, about 0.65%-0.85% by weight of colloidal silica, in another preferred embodiment, about 0.75% by weight of colloidal silica;

from about 1-20% by weight of mannitol (mannitol, USP), preferably from about 5-15% by weight of mannitol, in one preferred embodiment, about 7.5%-12.5% by weight of mannitol, in another preferred embodiment, about 10% by weight of mannitol;

from about 2-8% by weight of crospovidone (highly cross-linked modification of polyvinylpyrrolidone (PVP)), preferably from about 3-7% by weight of crospovidone, in one preferred embodiment, about 4-6% by weight of crospovidone, in another preferred embodiment, about 5% by weight of crospovidone; and, from about 0.45-1% by weight of magnesium stearate (Magnesium Stearate USP), preferably from about 0.55-0.95% by weight of magnesium stearate, in one preferred embodiment, about 0.65%-0.85% by weight of magnesium stearate, in another preferred embodiment, about 0.75% by weight of magnesium stearate.

In some embodiments, the abuse deterrent solid pharmaceutical dosage formulations are coated with a film coating. In some embodiments, the coating is a water-soluble, pH-independent film coating. Such coating allows for immediate disintegration for fast, active release of the contents of the solid dosage formulation. One such commercially available coating useful in the solid dosage formulations of the present disclosure is Opadry®, and preferably Opadry II®. In specific embodiments, the abuse deterrent solid pharmaceutical dosage formulations include a film coating present in an amount of from about 0.5-5.5% by weight film coating, preferably from about 1-5% by weight film coating, in one preferred embodiment, about 2-4% by weight film coating, in another preferred embodiment, about 3% by weight film coating.

In some instances, opioid receptor agonist drugs have been formulated and marketed with an opioid antagonist (such as the opioid antagonist naloxone), to render the formulation abuse resistant. The present invention is also based, at least in part, on the surprising discovery, that the formulations of the present disclosure have abuse deterrent characteristics. For example, such formulation is non-tamperable thereby limiting ease of isolation and purification of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid from the formulation. Thus, in specific embodiments of the present disclosure, the formulations are substantially free of naloxone. In related embodiments of the present disclosure, the formulations are completely free of naloxone. Such formulations are advantageous because they can provide effective abuse deterrence in the absence of naloxone.

The formulations can also optionally include an inert pharmaceutically acceptable dissolution-rate-modifying agent, a pharmaceutically acceptable plasticizer, a pharmaceutically acceptable coloring agent (e.g., FD&C Blue #1), a pharmaceutically acceptable opacifier (e.g., titanium dioxide), pharmaceutically acceptable anti-oxidant (e.g., tocopherol acetate), a pharmaceutically acceptable preservative, flavorants (e.g., saccharin and peppermint), neutralizing agents (e.g., sodium hydroxide), buffering agents (e.g., monobasic, or tribasic sodium phosphate), or combinations thereof. Preferably, these components are individually present at no more than about 1% of the final weight of the formulation, but the amount may vary depending on the other components of the formulation.

For preparing formulations of the present disclosure, such as tablets, 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid is mixed with one or more pharmaceutical excipients to form a solid preformulation composition containing, in preferred embodiments, a homogeneous mixture of the excipient(s) with the active ingredient. When referring to these preformulation compositions as "homogeneous," it is meant that the active ingredient are dispersed evenly throughout the composition so that the composition may be readily subdivided into equally effective unit dosage forms such as tablets or capsules. This solid preformulation is then subdivided into unit dosage forms of the type described above containing from, for example, about 10 to about 200 milligrams of the active ingredient.

According to one embodiment, a solid dosage formulation of the present disclosure is prepared by:

i) blending 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid with the pharmaceutically acceptable inert excipients: silicified microcrystalline cellulose, mannitol, colloidal silica and crospovidone;

ii) comilling the above blend with the addition of magnesium stearate;

iii) compressing the dry blend into suitably sized tablets, or filling into capsules.

According to another embodiment, a solid dosage formulation is prepared using direct compression, by:

i) blending 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid with the pharmaceutically acceptable inert excipients silicified microcrystalline cellulose, mannitol, colloidal silica, and crospovidone;

ii) lubricating the blend by the addition of magnesium stearate;

iii) compressing the blend into suitably sized tablets.

According to another embodiment, capsules may be formulated by:

i) blending 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid with the pharmaceutically acceptable inert excipients silicified microcrystalline cellulose, mannitol, colloidal silica, and crospovidone;

ii) lubricating the blend by the addition of magnesium stearate, iii) filling the blend into capsule shells.

According to another embodiment, capsules may also be formulated by:

i) blending 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid with the pharmaceutically acceptable inert excipients silicified microcrystalline cellulose, mannitol, colloidal silica, and crospovidone;

ii) comilling the above blend, iii) adding magnesium stearate to lubricate the blend, iv) filling the blend into capsule shells.

According to another embodiment, capsules may also be formulated by:

i) blending 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid with the pharmaceutically acceptable inert excipients silicified microcrystalline cellulose, mannitol, colloidal silica, and crospovidone;

ii) comilling the above blend, iii) adding magnesium stearate to lubricate the blend, iv) compressing the blend into tablets.

In these embodiments of preparing the dosage formulations of this disclosure, the tablets or capsules may be film coated and/or packaged in bulk or unit-dosage packaging (i.e. blister packaging).

The active ingredient in the formulations of the present disclosure are useful opioid receptor modulators. In particular, certain compounds are opioid receptor agonists useful in the treatment or amelioration of conditions such as pain and gastrointestinal disorders. Examples of pain intended to be within the scope of the present invention include, but are not limited to, centrally mediated pain, peripherally mediated pain, structural or soft tissue injury related pain, pain related to inflammation, progressive disease related pain, neuropathic pain and acute pain such as caused by acute injury, trauma or surgery, and chronic pain such as caused by neuropathic pain conditions, diabetic peripheral neuropathy, post-herpetic neuralgia, trigeminal neuralgia, post-stroke pain syndromes or cluster or migraine headaches. The active ingredient in the formulations of the present disclosure are preferably useful for treating or ameliorating abdominal pain. Examples of gastrointestinal disorders intended to be within the scope of this invention include, but are not limited to, diarrheic syndromes, motility disorders such as irritable bowel syndrome including diarrhea-predominant, constipation-predominant or alternating irritable bowel syndrome, and visceral pain and diarrhea associated with inflammatory bowel disease including ulcerative colitis and Crohn's disease.

Examples of gastrointestinal disorders where -({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid may be useful include constipation-predominant irritable bowel syndrome, post-operative ileus and constipation, including but not limited to the constipation associated with treatment of chronic pain with opiates. Modulation of more than one opioid receptor subtype is also useful as follows: a compound that is a mixed mu OR agonist and delta OR antagonist could have antidiarrheal properties without being profoundly constipating. A compound that is a mixed mu OR agonist and delta OR agonist are useful in cases of severe diarrhea that are refractory to treatment with pure mu OR agonists, or has additional utility in treating visceral pain associated with inflammation and diarrhea.

The daily dose of a solid dosage formulation of the present disclosure may be a dose that is therapeutically effective for the treatment of irritable bowel syndrome, preferably diarrhea-predominant irritable bowel syndrome, wherein a patient has an average decrease of daily WAP scores from the patient's baseline WAP (for example a baseline WAP score of ≥3.0 (on a 0-10 numerical rating scale, where 0 indicates no pain and 10 worst pain imaginable) of about ≥10%, preferably a decrease in WAP score of about ≥20%, more preferably a decrease in WAP score of about ≥30%. The daily dose of a dosage formulation of the present disclosure may be a dose that is therapeutically effective for the treatment of irritable bowel syndrome, preferably diarrhea-predominant irritable bowel syndrome, wherein a patient achieves an average BSS score (wherein 1 equals hard, lumpy stools and 7 equals watery, liquid stools) of between 2 and 5, preferably 3 or 4.

The daily dose of a solid dosage formulation of the present disclosure may be varied over a wide range from about 20 mg to about 7000 mg of the active ingredient per adult human per day; preferably the dose will be in the range of from about 50 mg to about 2100 mg of the active ingredient per adult human per day. For oral administration, the formulations are preferably provided in the form of film-coated tablets containing about 75, about 100 or about 200 milligrams, more preferably about 75 or about 100 milligrams, of the active ingredient for the symptomatic adjustment of the dosage to the subject to be treated. Advantageously, dosage formulations of the present disclosure may be administered in a single daily dose or the total daily dosage may be administered in divided doses of two, three or four times daily. If administered twice daily, each dose may be administered at about 6 hours to about 12 hours apart per day, preferably about 8 hours to about 12 hours apart per day, preferably about 10 hours to about 12 hours apart per day, preferably about 10 hours apart per day, or preferably about 12 hours apart per day. In these preferred embodiments, the total daily dose is administered twice daily.

In certain embodiments, these methods may include the administration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid in a formulation of this disclosure to the subject on an every-other-day (qod) dosing regimen, or on a thrice-weekly dosing regimen, or on a twice-weekly dosing regimen, or on a once-weekly dosing regimen.

In certain embodiments, these methods may include the administration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid in a formulation of this disclosure to the subject on a twice-monthly dosing regimen, or on a once-monthly dosing regimen.

In certain embodiments, these methods may include the administration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid in a formulation of this disclosure to the subject on an as-needed (prn) dosing regimen.

Thus, an embodiment provided by this disclosure is a method of treating or ameliorating an opioid receptor related disorder by administering a formulation of this disclosure to a subject in need of such treatment. In one embodiment, this administration may be made in the absence of the separate or concurrent administration of the opioid antagonist naloxone. In specific embodiments, these methods may include the administration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid to the subject in an amount between about 20 mg and about 200 mg, preferably about 75, about 100 or about 200 milligrams, more preferably about 75 or about 100 milligrams.

In another embodiment, this administration may be made in the absence of, prior to or concurrent with, the administration of food. In one embodiment, 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid is administered to the subject with one or more daily meals, more preferably with breakfast and dinner.

Another embodiment of the disclosure relates to any of the formulations of this disclosure for use in the treatment or amelioration of a condition mediated by an opioid receptor, for example, any pain and gastrointestinal disorders disclosed herein, preferably such as diarrheic syndromes, motility disorders including post-operative ileus and constipation, and visceral pain including post-operative pain, irritable bowel syndrome and inflammatory bowel disorders.

Another embodiment of the disclosure relates to the use of any of the formulations of this disclosure in the preparation of a medicament for the treatment or amelioration of a condition mediated by an opioid receptor, for example pain and gastrointestinal disorders disclosed herein, such as diarrheic syndromes, motility disorders including post-operative ileus and constipation, and visceral pain including post-operative pain, irritable bowel syndrome and inflammatory bowel disorders.

The disclosure now being generally described will be more readily understood by reference to the following examples, which are included merely for the purposes of illustration of certain aspects of the embodiments of the present disclosure. The examples are not intended to limit the disclosure, as one of skill in the art would recognize from the above teachings and the following examples that other techniques and methods can satisfy the claims and can be employed without departing from the scope of the claimed disclosure.

EXAMPLES

Example 1—Description and Composition of Two Formulations of Disclosure

Description of the Dosage Form

The active ingredient, 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid was formulated as 75-mg and 100-mg film-coated tablets. The formulation was composed of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid and the inactive components listed in Table 1.

Composition

TABLE 1

Composition of Tablets, 75-mg and 100-mg

| Component and Quality Standard (and Grade) | Function | Strength (label claim) | | | |
|---|---|---|---|---|---|
| | | 75 mg | | 100 mg | |
| | | Quantity per mg | % | Quantity per mg | % |
| Active ingredient | Active | 75 | 12.5 | 100 | 12.5 |
| Silicified Microcrystalline cellulose (HD90) (NF, Ph. Eur.) | Filler | 426 | 71.0 | 568 | 71.0 |
| Colloidal silica (NF, Ph. Eur.) | Glidant | 4.5 | 0.75 | 6 | 0.75 |
| Mannitol (USP, Ph. Eur.) | Filler | 60 | 10.0 | 80 | 10.0 |
| Crospovidone (PolyP XL10) (NF, Ph. Eur.) | Disintegrant | 30 | 5.0 | 40 | 5.0 |
| Magnesium stearate (NF, Ph. Eur.) | Lubricant | 4.5 | 0.75 | 6 | 0.75 |
| Nominal Tablet Weight | — | 600 | 100 | 800 | 100 |
| Opadry II 85F18422 (Company Specification) | Film coat | 18 | 3.0 | 24 | 3.0 |
| Purified water, USP | Film coat solvent | —$^a$ | — | —$^a$ | — |
| Total | — | 618 | — | 824 | — |

$^a$Removed during processing

Example 2—Description of One Manufacturing Process (and Process Controls)

The flow chart for the method of manufacture for the 75- and 100-mg oral tablets is presented in FIG. 1.

Description of the Manufacturing Process of FIG. 1.

1. Screen silicified microcrystalline cellulose, mannitol, crospovidone and colloidal silica through a 20 mesh screen and magnesium stearate through a 30 mesh screen.
2. Transfer the following into a 650-L tote bin: half of the silicified microcrystalline cellulose, all of the active ingredient, mannitol, colloidal silica, crospovidone, and the remaining half of silicified microcrystalline cellulose. Blend at 12 rpm for 10 minutes. Add the magnesium stearate, blend at 12 rpm for 5 minutes and sample.
3. Compress the tablets using a Stoke 34D tablet press or similar with a speed of 35-45 rpm. Collect samples throughout the compression run.
4. Prepare the coating suspension by dispersing the Opadry II 85F18422 in water and mixing. Apply the coating suspension with a spray gun at 300 g/min in a 48 inch Accela Cota coater with following parameters:

TABLE 2

Tablet Coating Parameters

| Coating Parameter | Setting |
|---|---|
| No. of Baffles | 4 |
| Number of Spray Guns | 4 |
| Spray Apparatus | Schlick (Module 9347-1535 with pattern and atomization adjustments) |
| Nozzle Diameter/Air Cap | 1.2 mm/Air Cap 4 mm |
| Delivery System | Peristalic Pump |
| Gun to Bed Distance$^a$ | 9" (8-11") |
| Set Point Delivery Rate$^a$ | 300 ± 50 g/min/4 Guns |
| Pan Speed$^a$ | 4.5 (4-8) rpm |
| Atomizing Air$^a$ | 30 ± 5 psi |
| Pattern Air$^a$ | 25 ± 5 psi |
| Inlet Air Temperature$^a$ | 60 ± 10° C. |
| Air Volume (Inlet)$^a$ | 1500 ± 500 cfm |

Guideline only - adjust as required to achieve a suitable coating process

5. Cool the tablets and store in tared, labeled high density polyethylene (HDPE) containers lined with double polyethylene bags with twist ties.
6. Prepare final packaging in ACLAR blisters or HDPE bottles.

Example 3—Abuse Liability Assessment of Oral Formulation

An abuse liability assessment was undertaken in rhesus monkeys to determine the doses and systemic exposure levels following acute intravenous administration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid that would provide a discriminative stimulus in morphine-conditioned monkeys and positive reinforcing effects (self-administration) in heroin-conditioned monkeys. The drug discrimination studies revealed that morphine-trained monkeys discriminated between saline at an IV dose of ≥10 mg/kg of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid. Self-administration studies revealed that in monkeys conditioned to self-administer heroin, 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid (3.2 mg/kg/IV infusion) provided reinforcement for self-administration. However, 1 mg/kg did not produce a signal in either morphine- or heroin-conditioned primates.

Thus, at least in animals, oral administration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid does not produce CNS effects that are prototypic of abused drugs. However, parenteral administration does appear to produce these effects. Typically, when this pattern of effects is observed in animals, it is recommended to conduct a human laboratory abuse potential study using both the therapeutic route (i.e., oral), as well as the IV route, which would represent a "worst case scenario."

In addition the recommendation to conduct in vitro studies to determine the ease and feasibility of preparing 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid for abuse through alternative routes of administration such as injection or snorting (e.g., in vitro extractability/tamperability studies). This is consistent with the draft "Guidance for Industry: Assessment of Abuse Potential of Drugs" (FDA, 2010). This example discloses the findings of such in vitro extractability/tamperability studies.

Based on the FDA guidance, a series of in vitro laboratory assessment studies were designed to explore the abuse potential of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid. Specific areas that were identified for laboratory assessment were as follows:
- Physical manipulations and pretreatment effects
- Aqueous and organic solvent extractions
- Syringeability assessments
- Simulated smoking assessments Laboratory experiments were targeted toward outcomes that could produce tampered product suitable for administration by alternate routes of administration including injection, intranasal administration and smoking. Experiment design began with a consideration of the physical and chemical properties of the 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid and formulation excipients. The solubility profile of the 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid has been characterized as ranging from "slightly soluble" (1-10 mg/mL) in water to "sparingly soluble" 10-33 mg/mL in acidic pH2 buffered solutions to "freely soluble" (100-1000 mg/mL) in 0.1N NaOH solution. Consequently, a core group of laboratory assessments were directed toward experiments that characterized the "extractability" of the 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid from the formulation matrix. The formulation tested was the 75 mg and 100 mg tablets described in Example 1, Table 1.

The first phase of the study consisted of assessing the formulation for ease of physical manipulation (e.g., crushing, film coating removal, and pretreatments), extractability with selected aqueous and organic solvents, effects of filtration on assay results, simulated smoking experiments, and syringeability.

It was determined that first phase assessments of physical manipulations (cutting/crushing/grinding assessments, pretreatment by freezing and heating, and coating removal), and simulated smoking experiments provided a clear and complete body of data on these topics and no further assessments were needed. The first phase assessments of extraction provided a basis for a second, formal phase study of exctractions from this formulation.

All assessments of these tablet formulations were performed with the 100 mg 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid dosage tablet (total tablet weight=824 mg) with the exception of physical manipulation experiments and the Time Course study which were performed with the 75 mg strength tablet. The two dosage strengths are dose proportional in relation to excipients (common blend) and have the same coating.

To assure production of reliable, accurate data, the experimental design of laboratory protocols included the following elements: use of sufficient replicates to assess method variability; inclusion of controls for comparison where appropriate; investigation over a broad range of chemical and physical conditions; verification of analytical methods; and use of independent laboratories to whom validated methodologies had been transferred.

A. Physical Manipulations and Pretreatments

The ease of cutting and crushing of the tablets was assessed with a range of readily available household items including razor blades, spoons, pliers, tablet crushers, hammer, rolling pin, and mortar and pestle. The effect of tablet pretreatment by freezing at −20° C. or heating at 100° C. was also assessed. Coating removal was assessed by rubbing tablets with wet paper towels.

Result Summary and Discussion

Although the tablets were slightly difficult to "crack", crushing could readily be accomplished with a variety of common household tools. Freezing or oven heating of the tablets did not affect tablet "crushability." Coating removal could be accomplished easily with a wet paper towel.

B. Extractions
Solvent Extraction

Experiments designed to simulate preparation of the tablets for injection were conducted by extracting a single powdered or intact tablet at 25° C. with 10 mL of solvent for 15, 30 and 60 minutes with aqueous- and organic-based solvents (water, 0.1M HCl, ethanol, hexane, pH 2.0 buffer, pH 4.0 buffer, pH 7.0 buffer, pH 10.0 buffer, saline, 10% ethanol, acetone, and isopropyl alcohol). The water and ethanol extractions were repeated at 95° C.

Result Summary and Discussion

Percent recoveries of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid for solvent extractions at 25° C. were variable with solvent type. Aqueous-based solvents were more efficient than non-polar organic solvents (e.g., hexane). Acidic and basic solvents were more efficient than water or ethanol. Unusual high recoveries of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid were observed unexpectedly for isopropyl alcohol (80% at 60 minutes/25° C., ground tablet) and water (118% at 60 minutes/95° C.). It was noted that these experiments were conducted with unfiltered aliquots leading to the suspicion that un-dissolved particles of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid were being transferred and dissolved in the HPLC media during analysis, thereby falsely raising the true percent of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid undergoing dissolution (extraction).

Effects of Filtration on 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic Acid Extractability With the suspicion that unfiltered extractions might be a combination of true extracted (dissolved) 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid and suspensions of undissolved material, additional extractions were performed to determine the effect of filtration. Extracts were first filtered through 0.45 μm PTFE filters prior to HPLC analysis. Single whole and ground tablets were extracted at 25° C. with 10 mL solvent for 15, 30 and 60 minutes with water, acetone, isopropyl alcohol, ethanol, pH 2.0 buffer, pH 4.0 buffer, pH 7.0 buffer, pH 10.0 buffer.

Result Summary and Discussion

Addition of the filtration step reduced recoveries for all solvents. The greatest decreases were observed with the organic solvents. A comparison of the percentage of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid extracted for ground tablets at 60 minutes (25° C. with 10 mL solvent) is shown in Table 3, below. Clearly, undissolved particles led to falsely increased estimates of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid recovery and considerable scatter in individual determinations.

TABLE 3

Comparison of the percentage of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid extracted from ground tablets

| Solvent | % Recovery, Unfiltered | % Recovery, Filtered |
|---|---|---|
| Water | 63 | 38 |
| Acetone | 30 | 2 |
| Isopropyl Alcohol | 80 | 0 |
| Ethanol | 52 | 5 |
| pH 2 Buffer | 103 | 36 |
| pH 4 Buffer | 58 | 12 |
| pH 7 Buffer | 81 | 22 |
| pH 10 Buffer | 100 | 33 |

C. Syringeability

Experiments were conducted to determine the syringeability of tablet extracts. These assessments were performed on the remainder of solutions (following aliquot removal for determination of percentage of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid recovery) produced in the first phase extractions at 25° C. Solutions were aspirated into disposable syringes equipped with 25 gauge needles.

Result Summary and Discussion

All solutions were successfully loaded into disposable syringes equipped with a 25 gauge needle indicating that extracted solutions offered no resistance to syringeability.

D. Simulated Smoking Assessment

Simulated smoking of the active ingredient was assessed by heating ground or intact tablets in a test tube fitted with an apparatus that collected vaporized 5-({[2-Amino-3-(4-carbamoyl-2,6-dimethyl-phenyl)-propionyl]-[-(4-phenyl-1H-imidazol-2-yl)-ethyl]-amino}-methyl)-2-methoxy-benzoic acid. As heat from a heating block was applied to the sealed test tube, air was drawn through the tube and over the surface of the heated product. The air exited through a collector cartridge (C18 Sep-Pak cartridge) situated over the heated product. Product was heated to 225° C. until the material was charred (usually approximately 5 minutes). Samples were heated for a total of 10 minutes. In addition, pure 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid was treated in the same manner. The capacity for the apparatus to collect vaporized 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid was verified with a series of tests involving passing a standard solution of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid through the cartridge, and testing for "breakthrough" with serially connected cartridges. Recoveries of standard amounts of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid reference material trapped by the collector were essentially quantitative. Heating ground and intact tablets with a torch to extremely high temperatures was also attempted followed by collection of vaporized material with a bubbler collector.

Result Summary and Discussion

Browning and charring was evident when tablets and ground product were heated to 225° C. in the heating block or to extreme heat with a torch. No detectable 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid was vaporized from ground or intact tablets when heated by either method. Only extremely minor traces of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid were vaporized when pure 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid was heated under the same conditions. Mass balance analysis was attempted by analyzing the remaining 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid in the heated test tubes. Generally, 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid recoveries from the heated tube were low likely indicating that heating under these conditions produced thermal decomposition of the 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid. Consequently, it seems safe to conclude that smoking is not a viable route of administration for the 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid.

E. Aqueous Solvent Extraction

Small volume extractions were conducted with various household solvents and buffers to simulate extraction procedures that might be used for preparation of solutions for injection. Extractions were performed on six replicates of ground and intact tablets at 25° C. and 95° C. with 10 mL of solvent for 10 minutes. The extractions were shaken on an orbital shaker at 100 rpm, and then aliquots were removed and filtered with 0.45 μm PTFE filters for HPLC analysis. The solvents utilized in these assessments were water, saline, vinegar, 0.1M HCl, 10% ethanol, 40% ethanol, pH 2.0 buffer, pH 4.0 buffer, pH 7.0 buffer, and pH 10.0 buffer. Results were expressed in Table 4 below as % recovery (% label claim) and as concentration (mg/mL).

Result Summary and Discussion

TABLE 4

Summary of mean results (n = 6) is shown in the table below.

| Solvent | ° C. Temp | % Recovery, Ground | % Recovery, Intact | Conc. (mg/mL), Ground | Conc. (mg/mL), Intact |
|---|---|---|---|---|---|
| Water | 25 | 22.1 | 16.4 | 2.2 | 1.6 |
|  | 95 | 39.9 | 38.7 | 4.0 | 3.9 |
| Saline | 25 | 13.7 | 17.0 | 1.4 | 1.7 |
|  | 95 | 38.9 | 61.4 | 3.9 | 6.1 |
| Vinegar | 25 | 80.0 | 24.2 | 8.0 | 2.4 |
|  | 95 | 77.7 | 77.9 | 7.8 | 7.8 |
| 0.1M HCl | 25 | 33.5 | 50.1 | 3.3 | 5.0 |
|  | 95 | 65.4 | 59.6 | 6.5 | 6.0 |
| 10% Ethanol | 25 | 19.3 | 12.6 | 1.9 | 1.3 |
|  | 95 | 80.9 | 70.8 | 8.1 | 7.1 |
| 40% Ethanol | 25 | 23.9 | 27.9 | 2.4 | 2.8 |
|  | 95 | 91.6 | 64.6 | 9.2 | 6.5 |
| pH 2 Buffer | 25 | 56.1 | 32.7 | 5.6 | 3.3 |
|  | 95 | 67.5 | 73.2 | 6.8 | 7.3 |
| pH 4 Buffer | 25 | 8.8 | 8.1 | 0.9 | 0.8 |
|  | 95 | 27.8 | 24.2 | 2.8 | 2.4 |
| pH 7 Buffer | 25 | 10.8 | 14.7 | 1.1 | 1.5 |
|  | 95 | 41.3 | 40.0 | 4.1 | 4.0 |
| pH 10 Buffer | 25 | 38.5 | 38.3 | 3.9 | 3.8 |
|  | 95 | 83.9 | 65.4 | 8.4 | 6.5 |

Although there was considerable variability among replicates, generally, the average amount of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid release (% recovery) was comparable between ground and intact tablets. As expected, extraction at near boiling conditions (95° C.) increased drug release. The most efficient solvents for extraction (>50%) of ground tablets at 25° C. were vinegar and pH 2 buffer. At elevated temperature, the solvents that allowed >50% recovery for ground product were vinegar, 0.1M HCl, 10% ethanol, 40% ethanol, pH 2 buffer, and pH 10 buffer. Extract concentrations of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid from ground and intact tablets across all conditions ranged from 0.8 mg/mL to 9.2 mg/mL.

F. Organic Solvent Extraction

This series of extractions was performed in a similar manner as the aqueous solvent extractions previously described. Ground and intact tablets were extracted in 10 mL of solvent for 10 minutes on an orbital shaker at 100 rpm. Aliquots were removed and filtered with 0.45 μm PTFE filters for HPLC analysis. The solvents utilized in these assessments were 95% ethanol, isopropyl alcohol, acetone and hexane.

Result Summary and Discussion

Organic solvent extraction of tablets was inefficient (<10%) across all conditions. The most efficient solvent utilized in this assessment was 95% ethanol that provided an average % recovery of 8.2% 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid (range, 6.0%-40.3%).

G. Syringe Evaluation

Extracted solutions remaining from the aqueous extractions were assessed for syringeability. In this assessment, a 10 mL syringe fitted with a 25 gauge needed was utilized to withdraw as much of the remaining 7 mL volume of extracted solution as possible into the syringe. A cotton ball was used to filter the solution by inserting the needle in the cotton ball during aspiration of the solution. The volume of solution successfully aspirated into the syringe was estimated and an aliquot was tested to determine the milligram amount of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid loaded into the syringe.

Result Summary and Discussion

Of the remaining 7 mL volume of solution remaining from extraction of a powdered tablet, the typical volume that could be loaded into a 10 mL syringe fitted with a 25 gauge needle (cotton ball filtration) was 4-5 mL of solution. Thus, the loss of available solution ranged from approximately 30% to 43% in this simulated assessment of preparing a solution for intravenous injection. The absolute amount of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid varied with the type of solvent. Overall, there was no evidence of resistance to syringeability in these assessments.

H. Multiple Tablet Extraction

This initial series of extractions was designed to assess the extraction efficiency of selected aqueous-based solvents for preparation of tablets for injection. The extractions were performed with water and 0.1M HCl on ground tablets with equivalent weight of 2 and 4 tablets. The extraction was conducted with 10 mL of solvent for 10 minutes on an orbital shaker at 100 rpm at 95° C. Following extraction, aliquots were removed and filtered with 0.45 µm PTFE filters for HPLC analysis. The rationale for the design of this study was that individuals might attempt to extract a larger dose of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid through the use of heat, larger volumes and possibly use of acidic media. Although 10 mL volume is large for injection purposes, it is plausible that such a volume might be attempted, especially given the limited solubility of the 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid. Also, it should be noted that although injection of a highly acid solution (0.1M HCl) would likely result in discomfort and tissue injury, some individuals may attempt such procedures.

Result Summary and Discussion

The mean extraction efficiencies and concentration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid in this extraction assessment are shown in Table 5.

TABLE 5

Mean extraction efficiencies of active ingredient in extraction assessment

| Solvent | Number of Tablet Equivalents | % Recovery | Concentration, mg/mL |
|---|---|---|---|
| Water | 2 | 41.2 | 8.2 |
|  | 4 | 22.4 | 9.0 |
| 0.1M HCl | 2 | 76.8 | 15.4 |
|  | 4 | 46.1 | 18.5 |

It would appear that both water and 0.1M HCl have nearly reached capacity for dissolution of the 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid under the two tablet equivalent extraction condition at 95° C. The effect of doubling the amount of potentially extractable 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid to four equivalents provided nearly equal concentrations of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid in both water and acid solution. At the same time, % recovery for the 4 tablet condition was approximately one-half of the two tablet condition indicating each solvent had reached a capacity limiting condition.

I. Large Volume Extraction

Given that the 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid exhibits limited solubility in some solvents, extraction with a larger volume might be attempted by individuals attempting to isolate the 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid for administration by non-intended routes. This extraction assessment was performed with ground and intact tablets. Extractions were conducted with 30 mL volume of solvents (water, 0.1M HCl, 10% ethanol, and 95% ethanol) at 25° C. for 10 minutes and 24 hours on an orbital shaker at 100 rpm, then filtered with a 0.45 µm PTFE filter for HPLC analysis.

Result Summary and Discussion

The mean extraction efficiencies and concentration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid in this extraction assessment are shown in Table 6 below.

TABLE 6

Extraction efficiencies of active ingredient in extraction assessment

| Solvent | Extraction Time | % Recovery, Ground | % Recovery, Intact | Conc. (mg/mL), Ground | Conc. (mg/mL), Intact |
|---|---|---|---|---|---|
| Water | 10 min | 19.8 | 0.9 | 0.7 | 0.03 |
|  | 24 hr | 22.1 | 18.4 | 0.8 | 0.7 |
| 0.1M HCl | 10 min | 67.6 | 2.9 | 2.3 | 0.1 |
|  | 24 hr | 68.1 | 35.9 | 2.5 | 1.3 |
| 10% Ethanol | 10 min | 26.7 | 5.1 | 0.9 | 0.2 |
|  | 24 hr | 28.8 | 47.7 | 1.1 | 1.8 |
| 95% Ethanol | 10 min | 27.0 | 0.06 | 0.9 | 0.0 |
|  | 24 hr | 29.9 | 5.8 | 1.1 | 0.2 |

There was little difference in percent recovery of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid from the ground tablet following a 10 minute extraction period as compared to extending the extraction period to 24 hours. In contrast, extraction of intact tablets for 10 minutes was considerably less efficient than for 24 hours. It is likely that the increased surface area of the ground material was responsible for the rapidness of the 10 minute extraction outcome. All concentrations of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid in the different solvent extracts were consistently <3 mg/mL.

J. Small Volume Extraction

Smaller volume extractions are commonly used by individuals attempting to prepare a solution for injection. Water and saline are commonly used solvents for injection and were included in this study. Although it seems unlikely that 0.1M HCl would be used as a solvent because of it toxic effects, it was included as a "worst-case scenario" in consideration of the solubility properties of the 5-({[2-Amino-3-(4-carbamoyl-2,6-dimethyl-phenyl)-propionyl]-[1-(4- phenyl-1H-imidazol-2-yl)-ethyl]-amino}-methyl)-2-methoxy-benzoic acid in the tablets. This extraction assessment was performed with ground and intact tablets. Extractions were conducted with 5 mL volume of solvents (water, saline, and 0.1M HCl) at 25° C. and 95° C. for 10 minutes and 24 hours on an orbital shaker at 100 rpm, then filtered with a 0.45 µm PTFE filter for HPLC analysis.

Result Summary and Discussion

The mean extraction efficiencies and concentration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid in this extraction assessment are shown in Table 7 below.

TABLE 7

Extraction efficiencies of active ingredient in extraction assessment

| Solvent | Temp., °C. | Extraction Time | % Recovery, Ground | % Recovery, Intact | Conc. (mg/mL), Ground | Conc. (mg/mL), Intact |
|---|---|---|---|---|---|---|
| Water | 25 | 10 min | 16.2 | 16.4 | 3.2 | 3.3 |
|  | 95 | 10 min | 34.7 | 32.4 | 6.9 | 6.5 |
|  | 25 | 24 hr | 17.1 | 17.2 | 3.4 | 3.5 |
|  | 95 | 24 hr | 28.3 | 25.9 | 5.7 | 5.2 |
| Saline | 25 | 10 min | 16.9 | 17.5 | 3.4 | 3.5 |
|  | 95 | 10 min | 46.2 | 41.0 | 9.2 | 8.2 |
|  | 25 | 24 hr | 17.6 | 17.7 | 3.5 | 3.6 |
|  | 95 | 24 hr | 24.1 | 23.5 | 4.8 | 4.7 |
| 0.1M HCl | 25 | 10 min | 100.6 | 86.2 | 20.1 | 17.2 |
|  | 95 | 10 min | 90.2 | 102.3 | 18.1 | 20.5 |
|  | 25 | 24 hr | 91.8 | 95.1 | 18.4 | 19.0 |
|  | 95 | 24 hr | 79.1 | 83.9 | 15.8 | 16.8 |

Increasing the extraction temperature from 25° C. to 95° C. enhanced recovery and solubility of the 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid in water and saline; however extending extraction time did not appear to extract additional drug. Concentration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid in water and saline was consistently <10 mg/mL. The use of 0.1M HCl substantially enhanced recovery (nearly quantitative) and concentration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid in solution although extraction for 24 hr at 95° C. appeared to produce loss of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid (decomposition). Concentrations of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid in the acid extracts were in the range of 16-21 mg/mL.

K. Filter Evaluation

With the discovery that suspensions of material containing 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid were falsely elevating measures of drug release and recovery, an assessment was performed to determine how different types of filtration systems might affect drug release measurements. Extractions were performed on ground and intact tablets. Extractions were conducted with 5 mL volume of solvent (water, 0.1M HCl, 10% ethanol and 95% ethanol) at 25° C. for 10 minutes on an orbital shaker at 100 rpm. Following extraction, extracts were filtered as follows: unfiltered (control); 0.45 µm PTFE filter; cotton ball filter; cigarette filter; and coffee paper filter.

Result Summary and Discussion

The mean extraction efficiencies and concentration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid in this extraction assessment are shown in Table 8 below.

TABLE 8

Extraction efficiencies of active ingredient in extraction assessment

| Solvent | Filter Type | % Recovery, Ground | % Recovery, Intact | Conc. (mg/mL), Ground | Conc. (mg/mL), Intact |
|---|---|---|---|---|---|
| Water | Unfiltered | 49.1 | 61.9 | 9.8 | 12.4 |
|  | 0.45 µm PTFE filter | 16.5 | 16.9 | 3.3 | 3.4 |
|  | Cotton Ball | 18.2 | 16.8 | 3.6 | 3.4 |
|  | Cigarette Filter | 18.5 | 16.9 | 3.7 | 3.4 |
|  | Coffee Filter | 16.8 | 17.1 | 3.4 | 3.4 |
| 0.1M HCl | Unfiltered | 74.3 | 83.2 | 14.9 | 16.6 |
|  | 0.45 µm PTFE filter | 76.7 | 87.4 | 15.3 | 17.5 |
|  | Cotton Ball | 56.6 | 86.3 | 11.3 | 17.3 |
|  | Cigarette Filter | 37.6 | 82.8 | 7.5 | 16.6 |
|  | Coffee Filter | 63.2 | 85.3 | 12.6 | 17.1 |
| 10% Ethanol | Unfiltered | 90.7 | 76.4 | 18.1 | 15.3 |
|  | 0.45 µm PTFE filter | 22.4 | 23.5 | 4.5 | 4.7 |
|  | Cotton Ball | 24.0 | 23.7 | 4.8 | 4.8 |
|  | Cigarette Filter | 24.9 | 24.4 | 5.0 | 4.9 |
|  |  | 22.6 | 22.9 | 4.5 | 4.6 |
| 95% Ethanol | Unfiltered | 62.0 | 0.1 | 12.4 | 0.03 |
|  | 0.45 µm PTFE filter | 7.3 | 0.1 | 1.5 | 0.02 |
|  | Cotton Ball | 26.7 | 0.04 | 5.3 | 0.01 |
|  | Cigarette Filter | 16.0 | 0.02 | 3.2 | 0.0 |
|  | Coffee Filter | 10.4 | 0.03 | 2.1 | 0.01 |

Filtration had a substantial effect on apparent drug release in extractions with solvents that exhibit limited solubility (i.e., water, 10% ethanol, 95% ethanol) for the 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid. Without filtration, the evidence appears persuasive that particle suspension was the cause of these differences. When suspensions were prepared for assay by HPLC, the 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid became soluble in the HPLC mobile phase and this accounted for the elevated "readings" (measurements). In contrast, extraction with 0.1M HCl showed little difference in drug release and recovery with or without filtration. Since the 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid exhibits considerably greater solubility in 0.1M HCl, there were not suspended particles that would have been filtered out. It should be noted that this somewhat unusual behavior (forming particle suspensions in solvents with limited solubility for the 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid) adds a source of considerable variability that would be highly dependent upon conditions employed during extraction. This unique property of the formulation is not expected to be easily discoverable by individuals that might attempt extraction with common household solvents.

The sustained amount of time that an extraction solvent is in contact with a formulation can substantially influence how much active is released (and dissolved in the extraction solvent). This is particularly true for actives that exhibit limited solubility in the chosen solvent. Review of data generated in the study involving extraction with 30 mL of solvent for 10 minutes and 24 hours generally indicated greater variability (% RSD) for the shorter extraction time compared to the 24 hour extraction. To assess the influence to extraction time, a detailed time course study was conducted to determine the impact of extraction time on data variability and on percent recovery of the 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid from the tablets.

Extractions were performed on single ground and intact tablets (75 mg strength). Extractions were conducted with 22.5 mL volume of solvent (water, 0.1M HCl, vinegar, and pH 7 buffer) at 25° C. and 95° C. on an orbital shaker at 100 rpm. A 2 mL aliquot was withdrawn at each time point. The time points were as follows: 10, 20, 30, 45 and 60 minutes, 4, 12, and 24 hours. Extracts were filtered with a 0.45 μm PTFE filter for HPLC analyses.

Result Summary and Discussion

The mean extraction efficiencies of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid over time and % RSD (n=6 replicates) in this extraction assessment are shown in the Table 9, below.

TABLE 9

Extraction efficiencies of active ingredient over time

| Time Vessel | 10 minutes | 20 minutes | 30 minutes | 45 minutes | 1 Hour | 4 Hours | 12 Hours | 24 Hours |
|---|---|---|---|---|---|---|---|---|
| Amount of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid released label claim (%) Water Ground - 25° C. | | | | | | | | |
| Mean | 27.21 | 30.10 | 31.45 | 33.55 | 35.51 | 44.16 | 53.07 | 59.37 |
| RSD | 28.6 | 21.7 | 19.0 | 21.7 | 16.3 | 15.7 | 13.5 | 11.0 |
| Amount of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid released label claim (%) Water Whole - 25° C. | | | | | | | | |
| Mean | 2.04 | 12.59 | 18.75 | 20.86 | 25.40 | 36.81 | 51.21 | 55.07 |
| RSD | 43.8 | 63.7 | 32.8 | 38.2 | 24.6 | 11.8 | 4.6 | 4.0 |
| Amount of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid released label claim (%) Water Ground - 95° C. | | | | | | | | |
| Mean | 56.90 | 64.63 | 70.42 | 75.04 | 81.27 | 91.07 | 94.43 | 94.42 |
| RSD | 45.1 | 33.9 | 26.6 | 20.6 | 14.4 | 4.4 | 3.6 | 3.0 |
| Amount of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid released label claim (%) Water Whole - 95° C. | | | | | | | | |
| Mean | 80.78 | 83.66 | 84.16 | 87.39 | 89.43 | 93.21 | 93.11 | 93.32 |
| RSD | 6.5 | 5.8 | 5.1 | 5.1 | 4.8 | 3.3 | 3.9 | 3.0 |
| Amount of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid released label claim (%) 0.1M HCl Ground - 25° C. | | | | | | | | |
| Mean | 87.33 | 89.02 | 91.07 | 93.50 | 92.99 | 97.84 | 101.50 | 101.39 |
| RSD | 30.5 | 30.2 | 24.7 | 17.2 | 18.3 | 7.3 | 1.9 | 2.0 |
| Amount of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid released label claim (%) 0.1M HCl Whole - 25° C. | | | | | | | | |
| Mean | 2.69 | 14.32 | 31.30 | 35.88 | 59.16 | 77.52 | 101.48 | 102.69 |
| RSD | 51.7 | 72.2 | 44.5 | 21.8 | 19.5 | 9.4 | 1.9 | 2.8 |
| Amount of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid released label claim (%) 0.1M HCl Ground - 95° C. | | | | | | | | |
| Mean | 99.59 | 95.96 | 97.03 | 96.96 | 97.30 | 94.15 | 86.08 | 77.39 |
| RSD | 1.9 | 2.1 | 2.0 | 2.2 | 2.3 | 2.3 | 2.4 | 2.5 |
| Amount of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid released label claim (%) 0.1M HCl Whole - 95° C. | | | | | | | | |
| Mean | 48.15 | 71.95 | 81.70 | 89.30 | 93.49 | 100.44 | 93.17 | 82.24 |
| RSD | 17.7 | 8.3 | 5.1 | 4.6 | 2.9 | 3.1 | 1.8 | 2.6 |
| Amount of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid released label claim (%) Vinegar Ground - 25° C. | | | | | | | | |
| Mean | 88.42 | 88.76 | 90.61 | 91.82 | 93.93 | 98.38 | 100.89 | 101.12 |
| RSD | 3.6 | 4.2 | 3.3 | 4.3 | 5.3 | 2.5 | 1.8 | 1.4 |

TABLE 9-continued

Extraction efficiencies of active ingredient over time

| Time Vessel | 10 minutes | 20 minutes | 30 minutes | 45 minutes | 1 Hour | 4 Hours | 12 Hours | 24 Hours |
|---|---|---|---|---|---|---|---|---|
| Amount of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid released label claim (%) Vinegar Whole - 25° C. | | | | | | | | |
| Mean | 17.12 | 18.23 | 20.04 | 35.03 | 42.72 | 58.04 | 101.52 | 105.46 |
| RSD | 207.3 | 171.5 | 158.6 | 97.4 | 67.5 | 36.9 | 5.3 | 2.7 |
| Amount of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid released label claim (%) Vinegar Ground - 95° C. | | | | | | | | |
| Mean | 94.28 | 98.54 | 100.73 | 101.69 | 103.65 | 105.12 | 104.81 | 102.88 |
| RSD | 11.0 | 8.6 | 7.3 | 5.4 | 4.6 | 4.0 | 4.5 | 4.4 |
| Amount of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid released label claim (%) Vinegar Whole - 95° C. | | | | | | | | |
| Mean | 40.62 | 55.03 | 83.87 | 91.96 | 97.91 | 111.12 | 111.29 | 109.85 |
| RSD | 4.1 | 8.9 | 23.7 | 16.5 | 10.8 | 4.7 | 4.5 | 5.6 |
| Amount of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid released label claim (%) pH 7 Ground - 25° C. | | | | | | | | |
| Mean | 39.81 | 44.07 | 47.83 | 50.48 | 52.76 | 59.47 | 68.50 | 76.49 |
| RSD | 7.5 | 10.7 | 16.1 | 15.7 | 15.1 | 14.4 | 8.8 | 7.9 |
| Amount of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid released label claim (%) pH 7 Whole - 25° C. | | | | | | | | |
| Mean | 3.50 | 6.21 | 9.15 | 10.25 | 13.68 | 22.74 | 42.44 | 54.14 |
| RSD | 32.5 | 67.3 | 65.5 | 41.9 | 15.7 | 18.7 | 16.3 | 10.0 |
| Amount of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid released label claim (%) pH 7 Ground - 95° C. | | | | | | | | |
| Mean | 58.27 | 77.50 | 82.71 | 87.58 | 90.99 | 98.74 | 98.87 | 96.37 |
| RSD | 23.3 | 13.8 | 9.6 | 5.7 | 4.3 | 5.4 | 4.9 | 5.0 |
| Amount of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid released label claim (%) pH 7 Whole - 95° C. | | | | | | | | |
| Mean | 51.73 | 67.29 | 74.12 | 77.83 | 81.70 | 97.02 | 100.80 | 97.68 |
| RSD | 17.1 | 4.3 | 7.4 | 2.4 | 2.8 | 4.0 | 3.4 | 3.5 |

An analysis of the mean % RSD from these data across the four solvents is shown in the Table 10 below.

TABLE 10

Mean % RSD across the four solvents

| Time, hr | Mean % RSD 25° C. Ground | Mean % RSD 25° C. Whole | Mean % RSD 95° C. Ground | Mean % RSD 95° C. Whole |
|---|---|---|---|---|
| 0.17 | 17.6 | 83.8 | 20.3 | 11.4 |
| 0.33 | 16.7 | 93.7 | 14.6 | 6.8 |
| 0.5 | 15.8 | 75.4 | 11.4 | 10.3 |
| 0.75 | 14.7 | 49.8 | 8.5 | 7.2 |
| 1 | 13.8 | 31.8 | 6.4 | 5.3 |
| 4 | 10.0 | 19.2 | 4.0 | 3.8 |
| 12 | 6.5 | 7.0 | 3.9 | 3.4 |
| 24 | 5.6 | 4.9 | 3.7 | 3.7 |

In general, there was greater variability in extraction of the 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid from the tablets with shorter times and at the lower extraction temperature (25° C.) compared to 95° C. Also, there was less variability in extraction of the ground tablet at 25° C. compared to the whole tablet.

Figure 2:
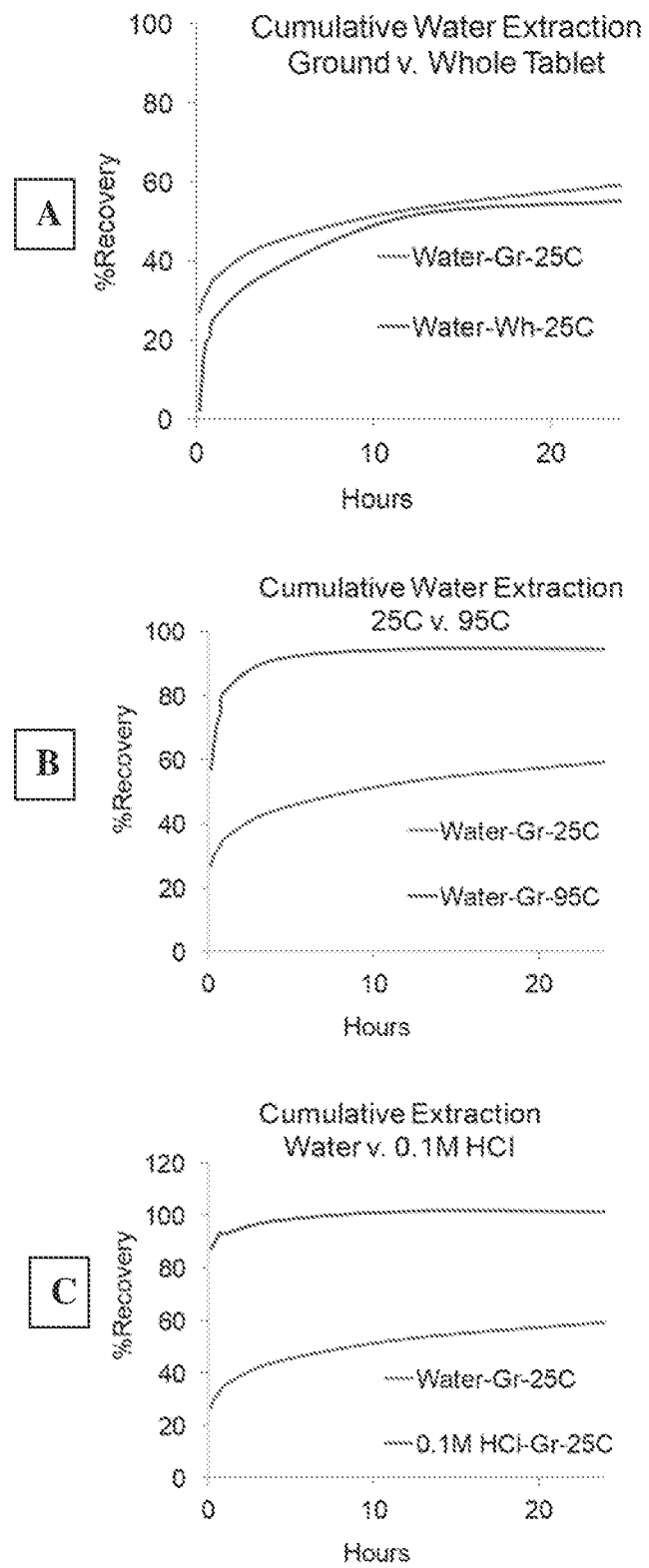
FIG. 2, shows representative time course plots of cumulative percent recovery of active ingredient under different extraction conditions: A, ground vs. whole tablet; B, 25° C. vs. 95° C.; C, water vs. 0.1M HCl.

Representative time course plots of cumulative percent recovery of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid under different extraction conditions are shown in FIG. 2. The abbreviations used in the plots are as follows:

Gr=ground tablet; Wh=whole, intact tablet.

General observations from these time course data include the following:

With short extraction times (e.g., 10 minutes), ground tablets are more efficiently extracted than whole tablets With extended extraction time (e.g., 24 hours), there is little difference in extractability of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid from ground versus whole tablets Extraction under heated conditions (e.g., 95° C.) substantially increases % recovery at shorter extraction times Acidic solvents are more efficient in extracting 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid than water or pH neutral solvents L. Investigations of Multiple Tablet Extractions In addition to extractions of multiple tablets, additional experiments were conducted to determine the optimal conditions for preparation of multiple tablets for injection. Initially, attempts were made to identify the correct combination(s) of solvent and ground tablets that would yield the most concentrated recoverable solution of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid from tablets. Based on these initial assessments, a study was designed in which extractions were conducted with powdered tablets at 25° C. and 95° C. with the equivalent of four tablets. The extractions were conducted for 10 minutes, one hour, and 12 hours with 10 mL of water, vinegar, 0.1M HCl, and saline. The extraction vials were shaken on an orbital shaker at 200 rpm. Following extraction, extracts were filtered with a 0.45 μm PTFE filter for HPLC analyses.

Result Summary and Discussion

The mean extraction efficiencies and concentrations of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid over time in this extraction assessment are shown in Table 11 below. Data for the four solvents are listed in order from lowest (water) to highest polarity and acidity (0.1M HCl).

TABLE 11

Extraction efficiencies and concentrations of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid over time

| Solvent | Extraction Time | % Recovery, 25° C. | Conc. (mg/mL), 25° C. | % Recovery, 95° C. | Conc. (mg/mL), 95° C. |
|---|---|---|---|---|---|
| Water | 10 min | 8.1 | 3.3 | 24.2 | 9.7 |
|  | 1 hr | 9.5 | 3.8 | 23.6 | 9.4 |
|  | 12 hr | 8.9 | 3.6 | 25.1 | 10.0 |
| Saline | 10 min | 8.9 | 3.5 | 18.5 | 7.4 |
|  | 1 hr | 9.8 | 3.9 | 22.3 | 8.9 |
|  | 12 hr | 9.8 | 3.9 | 24.1 | 9.6 |
| Vinegar | 10 min | 5.6 | 2.2 | 16.0 | 6.4 |
|  | 1 hr | 27.7 | 11.1 | 48.0 | 19.2 |
|  | 12 hr | 78.8 | 31.5 | 79.5 | 31.8 |
| 0.1M HCl | 10 min | 18.0 | 7.2 | 34.3 | 13.7 |
|  | 1 hr | 39.7 | 15.9 | 70.2 | 28.1 |
|  | 12 hr | 88.3 | 35.3 | 90.6 | 36.3 |

These data suggest that the maximal concentration of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid that can be extracted with water and saline is approximately 4 mg/mL at room temperature (e.g., 25° C.) and approximately 10 mg/mL under near boiling conditions (e.g., 95° C.). Further, there appeared to be little difference in maximal concentrations with water and saline regardless of extraction time. Use of an acidic solvent such as vinegar and the highly acidic solvent, 0.1M HCl led to the production of more concentrated extracts of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid with maximal values of approximately 36 mg/mL being achieved with a 12 hour extraction period. There was both time and temperature dependence on concentration with these two solvents. With vinegar, maximal concentrations over the 10 minute and one hour extraction period were approximately 2-11 mg/mL at 25° C. and 6-19 mg/mL, respectively. With 0.1M HCl, maximal concentrations over the 10 minute and one hour extraction period were approximately 7-16 mg/mL at 25° C. and 14-28 mg/mL, respectively. Given these maximal concentrations, an estimate of the required volume of extracted 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid that would deliver 350 mg of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid by injection is shown in Table 12 below.

TABLE 12

Estimate of the required volume of extracted 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid that would deliver 350 mg of active ingredient by injection.

| Solvent | Extraction Time | Conc. (mg/mL), 25° C. | Injection Volume (mL) Required for 350 mg of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid at 25° C. | Conc. (mg/mL), 95° C. | Injection Volume (mL) Required for 350 mg of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid at 95° C. |
|---|---|---|---|---|---|
| Water | 10 min | 3.3 | 106.1 | 9.7 | 36.1 |
|  | 1 hr | 3.8 | 92.1 | 9.4 | 37.2 |
|  | 12 hr | 3.6 | 97.2 | 10 | 35.0 |
| Saline | 10 min | 3.5 | 100.0 | 7.4 | 47.3 |
|  | 1 hr | 3.9 | 89.7 | 8.9 | 39.3 |
|  | 12 hr | 3.9 | 89.7 | 9.6 | 36.5 |
| Vinegar | 10 min | 2.2 | 159.1 | 6.4 | 54.7 |
|  | 1 hr | 11.1 | 31.5 | 19.2 | 18.2 |
|  | 12 hr | 31.5 | 11.1 | 31.8 | 11.0 |
| 0.1M HCl | 10 min | 7.2 | 48.6 | 13.7 | 25.5 |
|  | 1 hr | 15.9 | 22.0 | 28.1 | 12.5 |
|  | 12 hr | 35.3 | 9.9 | 36.3 | 9.6 |

Typical opioid injection volumes are generally in the 1-3 mL range but plausibly could be as high as 10 mL. Assuming that a 350 mg injected dose of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid would be required to produce a euphoric effect, it does not appear feasible that tablets could be prepared for injection with sufficient content of 5-({[2-Amino-3-(4-carbamoyl-2, 6-dimethyl-phenyl)-propionyl]-[1-(4-phenyl-1H-imidazol-2-yl)-ethyl]-amino}-methyl)-2-methoxy-benzoic acid when using typical injection solvents (water, saline). Although a sufficiently concentrated solution of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid by extraction does appear to be possible through the use of vinegar and 0.1M HCl, it is unlikely that many individuals would be willing to accept the potential toxic risks that these solvents present.

The foregoing examples of the present disclosure have been presented for purposes of illustration and description. Furthermore, these examples are not intended to limit the disclosure to the form disclosed herein. Consequently, variations and modifications commensurate with the teachings of the description of the disclosure, and the skill or knowledge of the relevant art, are within the scope of the present disclosure. The specific embodiments described in the examples provided herein are intended to further explain the best mode known for practicing the disclosure and to enable others skilled in the art to utilize the disclosure in such, or other, embodiments and with various modifications required by the particular applications or uses of the present disclosure. It is intended that the appended claims be construed to include alternative embodiments to the extent permitted by the prior art.

What is claimed is:

1. A pharmaceutical tablet comprising:
   about 75 mg or about 100 mg of 5-({[(2S)-2-Amino-3-(4-carbamoyl-2,6-dimethyl-phenyl)-propionyl]-[(1S)-1-(4-phenyl-1H-imidazol-2-yl)-ethyl]-amino}-methyl)-2-methoxy-benzoic acid;
   about 70-90% by weight of a combination of a first filler and a second filler;
   about 3-7% by weight disintegrant;
   about 0.55-0.95% by weight colloidal silicon dioxide; and
   about 0.45-1% by weight lubricant;
   wherein the first filler is mannitol; and wherein the tablet comprises at least 10% by weight mannitol.

2. The tablet of claim 1, wherein the second filler is silicified microcrystalline cellulose.

3. The tablet of claim 1, wherein the disintegrant is crospovidone.

4. The tablet of claim 1, comprising about 5% by weight disintegrant.

5. The tablet of claim 4, comprising about 100 mg of 5-({[(2S)-2-Amino-3-(4-carbamoyl-2,6-dimethyl-phenyl)-propionyl]-[(1S)-1-(4-phenyl-1H-imidazol-2-yl)-ethyl]-amino}-methyl)-2-methoxy-benzoic acid.

6. The tablet of claim 5, comprising about 0.75% by weight colloidal silicon dioxide and about 0.75% by weight lubricant, wherein the lubricant is magnesium stearate.

7. The tablet of claim 5, wherein the disintegrant is crospovidone.

8. The tablet of claim 7, comprising about 0.75% by weight colloidal silicon dioxide and about 0.75% by weight lubricant.

9. The tablet of claim 8, wherein the lubricant is magnesium stearate.

10. The tablet of claim 1, comprising:
    about 100 mg of 5-({[(2S)-2-Amino-3-(4-carbamoyl-2,6-dimethyl-phenyl)-propionyl]-[(1S)-1-(4-phenyl-1H-imidazol-2-yl)-ethyl]-amino}-methyl)-2-methoxy-benzoic acid;
    about 560 mg-720 mg of the combination of the first filler and the second filler;
    about 24 mg-56 mg disintegrant;
    about 4.4 mg-7.6 mg colloidal silicon dioxide; and
    about 3.6 mg-8 mg lubricant;
    wherein the first filler is mannitol; and wherein the tablet comprises at least 80 mg mannitol.

11. The tablet of claim 10, comprising about 40 mg disintegrant.

12. The tablet of claim 11, comprising about 6 mg colloidal silicon dioxide and about 6 mg lubricant, wherein the lubricant is magnesium stearate.

13. The tablet of claim 11, wherein the disintegrant is crospovidone.

14. The tablet of claim 13, comprising about 6 mg colloidal silicon dioxide and about 6 mg lubricant.

15. The tablet of claim 14, wherein the lubricant is magnesium stearate.

16. The tablet of claim 4, comprising about 75 mg of 5-({[(2S)-2-Amino-3-(4-carbamoyl-2,6-dimethyl-phenyl)-propionyl]-[(1S)-1-(4-phenyl-1H-imidazol-2-yl)-ethyl]-amino}-methyl)-2-methoxy-benzoic acid.

17. The tablet of claim 16, comprising about 0.75% by weight colloidal silicon dioxide and about 0.75% by weight lubricant.

18. The tablet of claim 17, wherein the lubricant is magnesium stearate.

19. The tablet of claim 16, wherein the disintegrant is crospovidone.

20. The tablet of claim 19, comprising about 0.75% by weight colloidal silicon dioxide and about 0.75% by weight lubricant.

21. The tablet of claim 20, wherein the lubricant is magnesium stearate.

22. The tablet of claim 1, comprising:
    about 75 mg of 5-({[(2S)-2-Amino-3-(4-carbamoyl-2,6-dimethyl-phenyl)-propionyl]-[(1S)-1-(4-phenyl-1H-imidazol-2-yl)-ethyl]-amino}-methyl)-2-methoxy-benzoic acid;
    about 420 mg-540 mg of the combination of the first filler and the second filler;
    about 24 mg-42 mg disintegrant;
    about 3.3 mg-5.7 mg colloidal silicon dioxide; and
    about 2.7 mg-6 mg lubricant, wherein the lubricant is magnesium stearate;
    wherein the first filler is mannitol; and wherein the tablet comprises at least 10% by weight mannitol.

23. The tablet of claim 22, comprising about 40 mg disintegrant.

24. The tablet of claim 23, comprising about 4.5 mg colloidal silicon dioxide and about 4.5 mg magnesium stearate.

25. The tablet of claim 22, comprising about 30 mg disintegrant, wherein the disintegrant is crospovidone.

26. The tablet of claim 25, comprising about 4.5 mg colloidal silicon dioxide and about 4.5 mg of magnesium stearate.

27. A pharmaceutical tablet comprising:
    about 75 mg or about 100 mg of 5-({[(2S)-2-Amino-3-(4-carbamoyl-2,6-dimethyl-phenyl)-propionyl]-[(1S)-1-(4-phenyl-1H-imidazol-2-yl)-ethyl]-amino}-methyl)-2-methoxy-benzoic acid;

about 60-80% by weight filler;
about 7.5-12.5% by weight mannitol;
about 3-7% by weight disintegrant;
colloidal silicon dioxide; and
about 0.45-1% by weight magnesium stearate.

28. The tablet of claim 27, wherein the filler is silicified microcrystalline cellulose and the tablet comprises about 0.55-0.95% by weight colloidal silicon dioxide.

29. The tablet of claim 28, wherein the disintegrant is crospovidone.

30. The tablet of claim 27, wherein the filler is silica fine microcrystalline cellulose and the disintegrant is crospovidone.

* * * * *